(12) United States Patent
Rein et al.

(10) Patent No.: US 7,604,598 B2
(45) Date of Patent: Oct. 20, 2009

(54) APPARATUS, SYSTEM AND METHOD FOR EVALUATION OF ESOPHAGEAL FUNCTION

(75) Inventors: Azaria J J T Rein, Jerusalem (IL); Michael Lysiansky, Ramat Gan (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 654 days.

(21) Appl. No.: 10/996,188

(22) Filed: Nov. 22, 2004

(65) Prior Publication Data
US 2005/0124888 A1    Jun. 9, 2005

Related U.S. Application Data

(63) Continuation of application No. PCT/IL03/00423, filed on May 22, 2003.

(30) Foreign Application Priority Data
May 23, 2002   (IL) ..................... 149844

(51) Int. Cl.
*A61B 8/00*   (2006.01)
(52) U.S. Cl. .............. 600/443; 600/407; 600/437; 600/454; 600/455; 600/468; 606/140
(58) Field of Classification Search ......... 600/437–472, 600/407, 547, 412; 606/140
See application file for complete search history.

(56) References Cited

U.S. PATENT DOCUMENTS

| | | | |
|---|---|---|---|
| 4,316,391 A | 2/1982 | Tickner | |
| 4,582,067 A * | 4/1986 | Silverstein et al. | 600/455 |
| 4,770,185 A * | 9/1988 | Silverstein et al. | 600/454 |
| 4,913,642 A | 4/1990 | Weber | |
| 5,601,086 A | 2/1997 | Pretlow, III et al. | |
| 5,701,898 A * | 12/1997 | Adam et al. | 600/454 |
| 5,878,749 A * | 3/1999 | Miller | 128/898 |
| 6,053,869 A | 4/2000 | Kawagishi et al. | |
| 6,450,946 B1 * | 9/2002 | Forsell | 600/37 |
| 6,695,764 B2 * | 2/2004 | Silverman et al. | 600/29 |
| 6,735,477 B2 * | 5/2004 | Levine | 607/58 |
| 7,074,189 B1 * | 7/2006 | Montegrande | 600/462 |

(Continued)

FOREIGN PATENT DOCUMENTS

EP    0 880 937 B1    12/1998

OTHER PUBLICATIONS

Nurko S, Esophageal Motility In: Walker WA, ed. Pediatric Gastrointestinal Disease, Philadelphia: Decker; 1991:224-235.

(Continued)

*Primary Examiner*—Brian Casler
*Assistant Examiner*—Joel M Lamprecht
(74) *Attorney, Agent, or Firm*—Martin Fleit; Paul D. Bianco; Fleit Gibbons Gutman Bongini & Bianco PL

(57) ABSTRACT

A method, system and apparatus for ultrasonically imaging boli that are swallowed, as they are passed through the esophagus. The trajectories of the boli are tracked, and image data corresponding to the esophagus thereby identified. Analysis of boli and esophagus image data enable esophageal parameters correlated thereto to be determined.

45 Claims, 24 Drawing Sheets

U.S. PATENT DOCUMENTS 7,217,245 B1 * 5/2007 Snow et al. .................. 600/549

OTHER PUBLICATIONS

Tygat GNJ, Gastro-Oesophageal Reflux and Gastric Stasis, Chester: Adis International; 1991.

Taber I, et al., Mechanism of gastroesophageal reflux in healthy premature infants, Journal of Pediatrics, 1998:650-655.

Yamazaki N, Principle of Doppler Tissue Velocity Measurements, In: Erbel R, Nesser HJ, Drozdz J, eds. Atlas of Tissue Doppler Echocardiography, Germany: Springer Press; 1995.

Strobel CT, Byme WJ, Ament ME, Euler AR, Correlation of esophageal lengths in children with height. Application to the Tuttle Test without prior esophageal manometry, J. Pediatr. 1979; 94:81-85.

Gryboski J, The swallowing mechanism of the neonate; Esophageal and gastric motility, Pediatrics, 1965;35:445-452.

Gomes H, Lallemand A, Lammemand P, Ultrasound of the gastroesophageal junction, Ped. Radiol., 1993;23:94-99.

Hirsch W, Keda R, Preiss U, Color Doppler in the diagnosis of gastroesophageal reflux in children: comparison with pH measurements and B-mode ultrasound, Pediatr. Radiol. 1996:26:232-235.

Jang HS, Lee SJ, Lim GY, Choy BG, Choi GH, Park HS, Correlation of color Doppler sonographic findings with pH measurements in gastoesophageal reflux in children, J. Clin. Ultrasound, 2001:29:212-217.

Takebayashi S, Matsui K, Ozawa Y, Nozawa T, Fujioka E, Cervical esophageal motility: Evaluation with ultrasound in progressive systemic scierosis, Radiology, 1991;179:389-393.

* cited by examiner

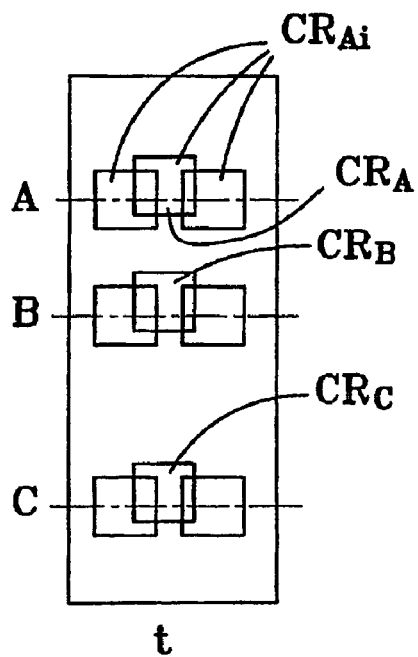
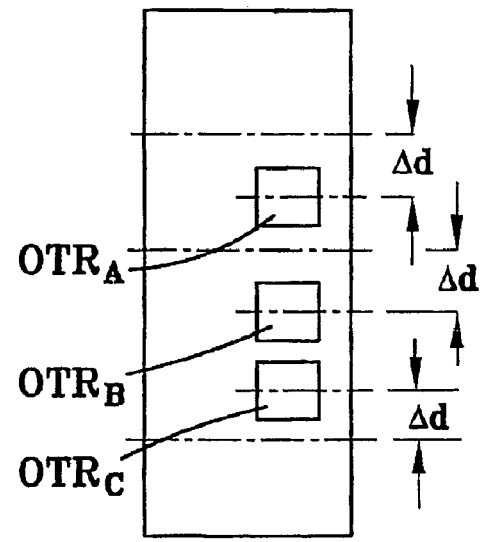
Fig. 26(a)     Fig. 26(b)
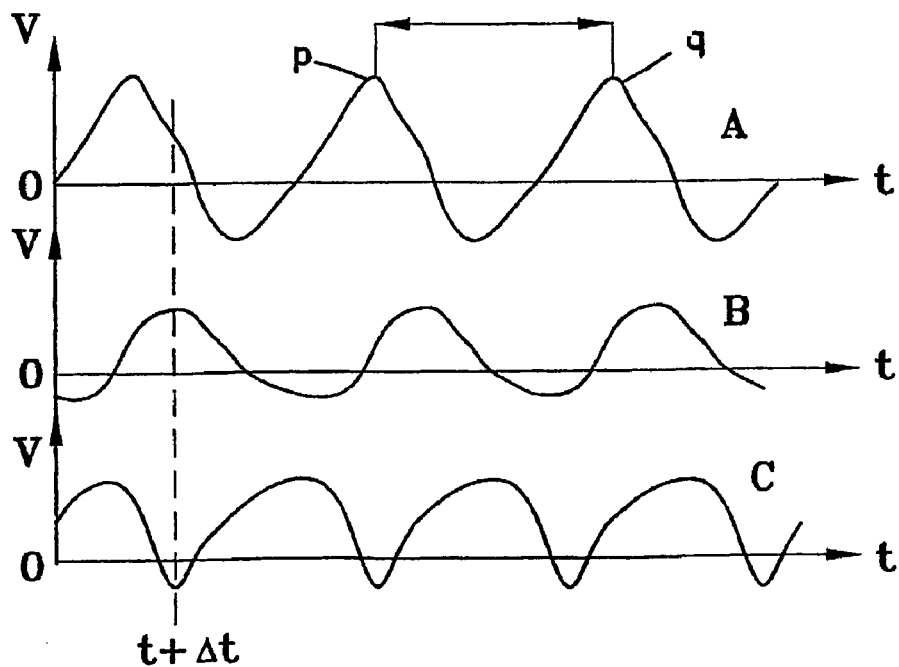
Fig. 27

2

APPARATUS, SYSTEM AND METHOD FOR EVALUATION OF ESOPHAGEAL FUNCTION

RELATED APPLICATION

This application is a continuation of International Application No. PCT/IL03/00423, filed May 22, 2003, the contents of which are here incorporated by reference in their entirety. The benefits of 35 USC Section 120 are claimed.

BACKGROUND OF THE INVENTION

1. Field of the Invention

The present invention is related to the field of medical imaging. More specifically the invention is related to the use of ultrasound for the evaluation of esophageal function, in particular by monitoring a food bolus via non-invasive means.

2. Prior Art

Publications and other reference materials referred to herein are incorporated herein by reference in their entirety and are numerically referenced in the following text and respectively grouped in the appended Bibliography which immediately precedes the claims.

The esophagus propels a swallowed bolus from the oropharynx to the stomach by means of rhythmic peristaltic waves. Normal function of the esophagus resides in the quality, in the amplitude, in the direction, and in the exact synchronized timing of these waves. The term "esophageal function" is herein taken to refer to the characteristics of the peristaltic motion or waves provided by the esophagus during swallowing and reflux, and thus the term "esophageal function parameter" relates to any suitable parameter that represents such motion. Thus, according to the present invention, the esophageal function parameters may be conveniently expressed as at least one of, and preferably all of the following:—propagation direction, inter-boli time and space intervals, velocity and acceleration of peristaltic waves. Preferably the boli are liquid, and thus substantially incompressible, and thus the boli propagation, inter-bolus time interval, and velocity are closely related to the equivalent peristaltic wave characteristics of the esophageal wall.

The functioning of the esophagus has been extensively studied using various methods, among them qualitative measurements (including barium swallow, esophageal scintiscanning, and ultrasound) and quantitative assessments (such as pH-metry and manometry). None of the methods used to date satisfies optimal requirements of safety, efficacy and non-invasiveness. For example, the "gold standard" for evaluating the esophagus is manometry [1,2], which uses continuously perfused low-compliance catheters. Manometry examinations evaluate motility waves through several preset manometric windows and therefore can provide only indirect measurement of the esophageal function as defined above. This procedure requires either the cooperation of the patient, so that regulated swallows may be registered, or a prolonged measurement as was made in a study in premature infants [3]. Especially with children, cooperation is difficult to obtain and sedation is usually needed. Moreover, there is no certainty that the mere insertion of a catheter and the continuous fluid perfusion do not alter the basic functions of the esophagus.

Barium swallow followed by radiography of the upper gastrointestinal tract is non-specific and inconclusive. It also involves X-ray radiation and major discomfort to the patient. Moreover, these methods do not allow repetition of the test in different conditions and thus preclude the assessment of anti-reflux medication or other therapeutic approaches.

Ultrasound is a bedside non-invasive and safe modality. A study using ultrasound can be performed during regular meals, does not require the patient's cooperation and may be repeated as necessary for follow-up or for the evaluation of medical treatment. Nevertheless, up to the present time, its application to qualitative assessment has not been possible.

Takebayashi [10] compared manometry measurements in adults suffering from progressive systemic sclerosis to Doppler measurements after swallowing soda water. As the study included adults only, it was anatomically limited to the cervical esophagus. Attempts to measure transit-time using a stopwatch failed, due to the short segment checked and to the low velocity of soda water. Beyond these limitations, Doppler ultrasound was found to be an effective means in the evaluation of motility in differentiating the normal from the pathologic esophagus in this very limited region of interest.

Gomes et al [7] compared the use of ultrasound, barium swallow and endoscopic studies in 300 children suffering from severe vomiting due to diaphragmatic hernia. The study proved the efficacy of ultrasound in regards to anatomic evaluation and patency of the lower esophageal sphincter, but did not include motility evaluation.

Hirsch et al [8] published in 1996 a study comparing the sensitivity of ultrasound and color Doppler versus pH-metry, which is considered the most sensitive test for evaluating gastro-esophageal reflux. In this study, the subject's stomach was filled with tea. The filling was done in a short time, in order to minimize the amount of gastric emptying, and then the refluxes were measured. In the case of some of the subjects of the study, the esophagus was bypassed by the use of a nasogastric tube to fill the stomach. Thus the study was focused on reflux and was not at all directed at evaluating the esophagus function neither qualitatively nor quantitatively, but rather preferred to bypass the esophagus altogether in some cases. In any case the technique employed was inappropriate for quantification of reflux velocities, as discussed in the paper.

A recent study by Jang et al [9] addressed the same issue but again provided qualitative data only on gastroesophageal reflux.

The search for an optimal method to use ultrasound techniques to evaluate the esophagus is an ongoing quest. In the prior art, conventional Doppler techniques, which are based on high motion or flow velocity measurements and low amplitude signals from the red blood cells, focus exclusively on body parts such as tissues, organs and blood vessels. For example, EP 880937 describes an ultrasonic diagnostic imaging method for tracking a characteristic (such as a tissue boundary) of moving tissue in a body, using a Doppler technique. Such methods are not considered suitable in the prior art for qualitative measurements of the esophagus function primarily due to the poor resolution of this organ with respect to surrounding tissue. Such methods would also be considered in the prior art to be unsuitable for monitoring a swallowed bolus because of the high acoustic backscattering and low velocity propagation associated therewith. While color sonography has been used to detect and "qualify" reflux episodes, no non-invasive method exists which quantifies and characterizes the esophageal function.

SUMMARY OF THE INVENTION

In contrast, the present invention is directed to the evaluation of the function of the esophagus by monitoring a swallowed bolus through the esophagus, and analyzing the characteristics of the bolus, rather than of the esophagus itself. The method of the present invention, as will become evident from the description herein, is not considered invasive since it can be carried out during regular eating or drinking by the patient, and does not strictly require any material to be ingested by the patient outside of normal eating. In other words the method of the invention can be performed during meal times, and does not require a special ingestion step. Furthermore, regular food is not considered invasive to the body, as it is a regular activity that is carried out regardless of any external investigation of the esophagus. Finally, the present invention relates a method for obtaining information from patients, and in general provides results which while useful do not on their own automatically enable a decision to be made on the treatment necessary to a patient if at all.

In one embodiment, tissue velocity imaging modality is utilized, which overcomes the limitations discussed above by filtering the low amplitude high velocity signal, leaving only high amplitude low velocity signals, which correspond to the acoustic characteristics of the bolus.

In a second embodiment of the invention, the boli are identified and tracked within the esophagus from ultrasonic image data, and the aforesaid parameters may be obtained therefrom.

It is therefore a purpose of the present invention to provide a method, system, and apparatus that overcome the limitations of the prior art and provide a non-invasive method which quantifies and characterizes the esophageal function.

It is another purpose of the present invention to provide a method, system, and apparatus that uses the motion of boli from a normal meal to quantify and characterize the esophageal function.

It is a further purpose of the present invention to provide a method, system, and apparatus that provide a non-invasive method which quantifies and characterizes the esophageal function and allows repetition of the tests in different conditions and thus allows the assessment of anti-reflux medication or other therapeutic approaches.

It is a further purpose of the present invention to provide an analysis unit that may be retrofitted or coupled to existing ultrasonic imaging systems for monitoring and analysis of the esophageal function.

Further purposes and advantages of this invention will appear as the description proceeds.

The present invention is thus directed to a method for monitoring passage of at least one food bolus through the esophagus whereby to evaluate the esophageal function of a patient, comprising the steps:
(a) acquiring ultrasonic image data of said at least one bolus at a plurality of temporal intervals as said at least one bolus passes through the esophagus after being swallowed by the patient;
(b) tracking said at least one bolus in said image data to identify esophagus and bolus image data corresponding to said bolus and to said esophagus in said image data;
(c) determining at least one esophagus function parameter from the said bolus and esophagus image data.

The present invention also relates to a method for evaluating the esophageal function of a patient when the patient is in the process of swallowing at least one food bolus via the esophagus, comprises the steps:
(d) acquiring ultrasonic image data of at least one bolus at a plurality of temporal intervals as said at least one bolus passes through the esophagus;
(e) tracking said at least one bolus in said image data to identify esophagus and bolus image data corresponding to the bolus and to said esophagus in said image data;
(f) determining at least one esophagus function parameter from the said bolus and esophagus image data.

Preferably, step (b) comprises the steps of:—
(e) determining global motion of the esophagus in the image data acquired in step (a);
(f) aligning image data in consecutive image data by correcting for the global motion determined in step (e);
(g) identifying esophagus image data by first identifying the position of the bolus image in successive images corresponding to the bolus traversing the esophagus.

Optionally, step (e) is preceded by the step:
(d) choosing a region of interest in said image data acquired in step (a), wherein step (e) is performed on the region of interest image data.

Step (e) may be performed by determining the global motion of a reference zone of the image data at said plurality of temporal intervals. The reference zone is preferably such that there is relatively insignificant relative movement between said reference zone and said esophagus in said image data.

The method preferably further comprises the step:—
(h) projecting the identified esophagus image data in step (g) to a polygonal image matrix, typically in the form of a rectangle.

Step (c) comprises the sub-steps:—
(j) obtaining one-dimensional image data corresponding to a line—preferably the mid-line—of the esophagus data obtained in step (h) for each esophagus image data along said plurality of temporal intervals;
(k) constructing an M-mode representation of the data provided in step (j);
(l) identifying trajectories of boli in said M-mode representation and determining at least one esophagus parameter therefrom, typically the velocity of said at least one bolus.

Alternatively, step (c) comprises the sub-steps:—
(m) choosing at least one station along one said esophagus image data frame;
(n) choosing at least one control zone at said at least one station;
(o) identifying a control zone in a subsequent esophagus image data frame having the closest image data to said at least one control zone of said station in (n);
(p) determining the displacement of the control zone in (n) and the identified control zone in (o);
(q) determining at least one esophagus parameter therefrom and/or from the time interval between said image data frame and said subsequent image data frame, such a parameter being typically the velocity, acceleration and/or inter-boli time interval, of said at least one bolus.

Step (o) may be performed by means of minimizing the SAD between the image of the control zone in (n) and the image of the identified control zone in (o).

Steps (m) to (q) are typically performed for each consecutive pair of esophagus image frames along the time domain.

In another embodiment of the invention, in step (a) said image data also comprises dynamic data for each said temporal interval. Such dynamic image data typically comprise Doppler velocity and is acquired by means of a Doppler technique.

In this embodiment, in step (b) bolus image data is identified by determining higher velocity regions of the image data, and these high velocity regions are visualized using a suitable colour-coded tissue velocity imaging technique. Step (c) may be performed substantially in real-time or off-line.

Step (b) may be carried out for a first portion of image motion data in (a) corresponding to an imaginary axis—preferably aligned with the longitudinal axis of the esophagus—within said image motion data recorded at each said time interval to provide velocity data along said axis. The first portion of said image motion data corresponding to said imaginary axis is compiled from each consecutive image data obtained at consecutive time intervals in step (a), to provide velocity data along said axis as a function of time. The position and trajectory of a bolus along the said axis with respect to time is correlated to portions of said velocity data having the relatively higher magnitudes of velocity among said velocity data. The average velocity of a bolus along said axis may be determined by identifying the trajectory of the bolus in said velocity data and providing the quotient of: (distance covered by the bolus along said axis) divided by (the corresponding time taken by the bolus). The position and trajectory of a number of consecutive boli along the said axis with respect to time is correlated to corresponding portions of said velocity data having the higher magnitudes of velocity among said velocity data. The inter-bolus distance and/or inter-boli time interval along said axis may be determined by identifying the trajectory of two consecutive boli in said velocity data and providing the distance between the two trajectories at any particular time interval within these trajectories.

Optionally, step (b) may be carried out for a second portion of image motion data in (a) corresponding to at least one predetermined location within said image motion data recorded at each said time interval to provide velocity data at said location. The said at least one location is located substantially on the longitudinal axis of the esophagus. The said second portion of said image motion data corresponding to said location is compiled from each consecutive image data obtained at consecutive time intervals in step (a)_to provide velocity data at said location as a function of time. The direction and velocity of boli passing through said location with respect to time may be correlated to portions of said velocity data having the relatively higher magnitudes of velocity among said velocity data. The peak velocity of a bolus passing through said location is determined by identifying a corresponding velocity peak in said velocity data. The mode of propagation of a number of consecutive boli at said location with respect to time is correlated to the integral of the velocity data with respect to time. The mode of propagation of the esophagus is deemed to be antegrade mode, retrograde mode and non-propulsive modes, according to whether the said integral is substantially positive, negative or zero, respectively.

The ultrasonic image motion data in step (b) is typically procured using a suitable tissue velocity imaging technique.

The esophagus function parameters comprise at least one, preferably more than one and more preferably all of the following: propagation direction, inter-boli time interval, inter-boli space interval, velocity and acceleration of peristaltic waves. The said boli are preferably liquid and thus substantially incompressible, wherein the boli propagation, inter-boli time interval, and velocity are particularly closely related to the equivalent peristaltic wave characteristics of the esophageal wall.

The present invention also relates to comparative methods for assessing the effect of a predetermined factor on the esophageal function of a patient, comprising:—
evaluating the esophageal function of said patient as described herein, wherein said food bolus initially swallowed by the patient conforms to a first condition;
repeating step (i) with the same method, but wherein the food bolus is now swallowed by the patient conforming to a second condition;
comparing the results obtained between steps (i) and (ii).

The comparative method may be applied particularly for assessing the effect of added medication on the esophageal function of a patient, comprising:—
evaluating the esophageal function of said patient according to the method described herein, wherein said food bolus of step (a) does not comprise said added medication;
repeating step (i), wherein the food bolus of step (a) now comprises said added medication;
comparing the results obtained between steps (i) and (ii).

The added medication may include, for example, at least one anti reflux medication.

The comparative method may also be applied particularly for assessing the effect of particular foodstuffs on the esophageal function of a patient, comprising:—
evaluating the esophageal function of said patient as described herein, wherein said food bolus initially swallowed by the patient comprises a datum foodstuff;
repeating step (i) with the same method, but wherein the food bolus now swallowed by the patient replaced by a bolus of the foodstuff being investigated;
comparing the results obtained between steps (i) and (ii).

In this comparative method, the foodstuff being investigated may include a new milk formula or cereal, for example.

The comparative method may also be applied particularly for assessing the effect of the position of the patient on the esophageal function of the patient, comprising:—
evaluating the esophageal function of said patient as described herein, wherein said food bolus is initially swallowed by the patient while in a first position;
repeating step (i) with the same method, but wherein the food bolus of preferably the same type of food is now swallowed by the patient while in a second position;
comparing the results obtained between steps (i) and (ii).

In this comparative method, the first position and the second position may include any one of sitting, lying down, standing, bending over, and the like.

The present invention also relates to a system for evaluating esophageal function of a patient, comprising an ultrasonic imaging system operatively connected to a suitable analysis unit, characterized in that the analysis unit is adapted for evaluating esophageal function according to the method described herein.

The present invention also relates to a device for evaluating esophageal function of a patient, comprising an ultrasonic imaging means having a operatively connected to a suitable analysis means, characterized in that the analysis means is adapted for evaluating esophageal function according to the method described herein.

While the present invention is based on conventional ultrasonic techniques, it nevertheless differs substantially in the manner in which these techniques are applied, and in how meaningful results relating to the esophagus are obtained. In conventional Doppler techniques, which are well known and need no further elaboration herein, backscattering from the tissues themselves is used for the determination of velocities in the tissue. For example, in conventional Doppler echocardiography, the backscattering from the red blood cells is analyzed and blood flow is then calculated from the Doppler velocity shift of red blood cells moving with the blood flow. In tissue velocity imaging, a recently introduced echocardiographic methodology analyses the backscattering of the myocardium and provides information on tissue motion velocity.

As opposed to many other organs, the walls of the esophagus are almost impossible to image with ultrasound. This is because the lungs, which surround the esophagus from its posterior and lateral aspect, are a very poor acoustic medium, i.e. there is not enough contrast with the surrounding tissue for successful imaging. Thus, conventional ultrasonic imaging methodologies, and also conventional Doppler methodologies, such as tissue velocity imaging, are unsuitable for directly determining esophageal wall motion.

In contrast to these conventional ultrasonic Doppler technologies, the structure analyzed by the present invention is not the blood flow (red blood cells) or the myocardium but a swallowed food bolus, which is of course not a body tissue. During deglutition the bolus propagation within the esophagus is sampled and analyzed, which in turn provides a measure of the esophageal function itself.

The name Doppler esophagography is used herein as a term for the method of the invention in order to distinguish between it and the conventional techniques on which it is based.

The process of acquisition and analysis of the data can be carried out in "real-time", "on-line". However, in the first embodiment of the invention, the method of Doppler esophagography analysis comprises two stages: first on-line acquisition of bolus propagation raw data and second off-line analysis of the raw data obtained in the first stage. The two stage approach is preferable mainly in order to shorten the amount of time necessary to acquire the data from the subject.

The method is carried out with a system comprising an ultrasound machine with capabilities of analysis of esophageal bolus velocity. Specific velocity and acoustic backscattering thresholding is employed in order to identify the bolus and separate it from the surrounding media. The bolus velocity data are then acquired and stored as raw-data.

Motion and velocity data cannot normally be analyzed using conventional ultrasound gray-scale image only. For ease in qualitative interpretation of the results, in one embodiment of the invention it is advantageous to color-encode the bolus velocity raw data for each pixel and to apply the color-coded information over the gray-scale image. With the waves classified as "antegrade" for those advancing from mouth to stomach, and "retrograde"—for those originating in the stomach or lower esophagus and progressing toward the mouth, the qualitative analysis of antegrade and retrograde (i.e. reflux) bolus propagation is based on the color encoded bolus velocity images.

The quantitative analysis of the bolus propagation is based on use of dedicated software which simultaneously analyzes the velocity amplitude of the bolus over multiple regions of interest located over the whole length of the visualized esophagus. In the first embodiment, Doppler velocity tracings of the bolus are obtained by sampling the propagating bolus from the raw data images. The distance of bolus propagation is calculated from the integral of the bolus velocity data over the time of its propagation. Wave-to-wave time intervals are also calculated from the raw data.

Acquisition of bolus velocity raw data takes from few seconds to a few minutes, depending upon the amount of data and specific questions asked by the clinician. Off-line data analysis takes few minutes.

In a second embodiment of the invention, Doppler velocity data is not required. Rather, standard ultrasonic image data may be obtained in the normal manner during a time period correlated with the passage of one or more boli through the esophagus. The individual boli are identified and tracked, and where necessary the global motion of the esophagus due to movement of the patient or the heart thereof, for example, or movement due to the respiratory process are compensated for. Motion parameters of the boli, such as velocity, direction, acceleration, interboli spacings and so on may be determined from the tracking of each bolus entity from frame to frame in the time domain.

All the above and other characteristics and advantages of the invention will be further understood through the following illustrative and non-limitative description of preferred embodiments thereof, with reference to the appended drawings.

BRIEF DESCRIPTION OF THE DRAWINGS

FIG. 16(a) and FIG. 16(b) graphically show the average velocities and the average accelerations, respectively, obtained at the beginning and end of the meal, in Example II.

FIGS. 26(a) and 26(b) schematically illustrate a method for determining velocities at specific stations along the esophagus.

FIG. 27 schematically illustrates velocity profiles obtained from FIGS. 26(a) and 26(b).

DETAILED DESCRIPTION OF PREFERRED EMBODIMENTS

The method of the invention is based on the study and analysis of food boli swallowed through the esophagus, typically, but not restricted to, during a normal meal. The invention provides a non-invasive method which analyzes the characteristics of propagation of the swallowed bolus, which progresses through the esophagus in a wave-like manner complementary to the peristaltic action of the esophagus. The characteristics of propagation of the food boli include the amplitude, the velocity and acceleration of the bolus wave, and provides information on timing and rhythmicity of the peristaltic waves that are responsible for the motion of the boli.

Figure 1:
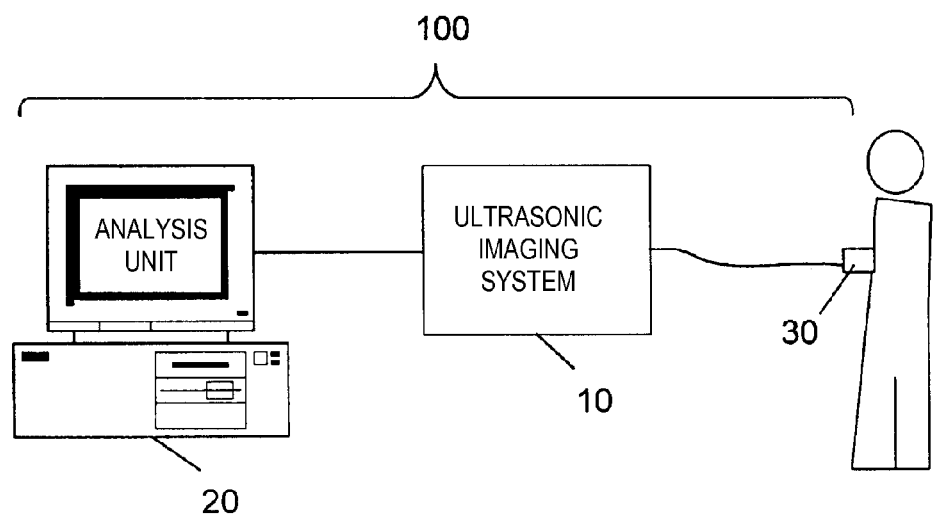
FIG. 1 schematically illustrates the main elements of the system according to a first embodiment of the present invention.

Referring to FIG. 1, and as will become clearer herein, the system of the present invention, generally designated by the numeral (100), comprises a suitable ultrasonic imaging system (10) coupled to a suitable analysis unit (20). The ultrasonic system (10) in the first embodiment is typically based on a Doppler Echocardiography system, and is characterized in being particularly adapted, or indeed dedicated, for providing image and motion data in the manner of the method of the present invention as described herein. The ultrasonic system (10) preferably comprises a selectable grey scale function capability, with the additional capability of measuring motion or velocity of the moving ultrasound image. The depth range for the ultrasonic system (10) is typically set at about 20 cm, for all patients, including adults, children and infants, with focal zone ranging from 2 cm to the end of the range. The frame acquisition rate is typically set at a minimum of 50 Hz (in TVI mode), and is typically in the range of about 50 Hz to about 200 Hz, although the range could include higher rates than 200 Hz and or lower rates than 50 Hz.

Tissue velocity Doppler imaging (TVI) is typically integrated in the ultrasonic system (10) with TVI colour coding for on-line visualization of boli propagation. The raw data provided by the ultrasonic system (10) is transmitted, typically via a suitable transducer having similar focus and depth capabilities as the ultrasonic system (10), to the analysis unit (20). The data is stored in the analysis unit (20), which is compatible with, and thus adapted for analyzing image data provided by the ultrasonic system (10), in the manner of the method of the present invention, as described herein. It is also possible to incorporate the said ultrasonic imaging system (10) and the analysis unit (20) into a single unitary device or apparatus. Thus the present invention also relates to such a device or apparatus comprising a suitable ultrasonic imaging means (corresponding to the said ultrasonic imaging system (10)) coupled to or otherwise operatively connected to a suitable data analysis means (corresponding to the said analysis unit (20)), preferably integrated into a unitary device or apparatus.

The method of the present invention, which is incorporated in the system and apparatus of the invention, is based on the study of the dynamics of food boli within the esophagus by means of ultrasonic imaging, manipulation and analysis of such imaging. The dynamics of the boli as they traverse the esophagus, including direction and velocity of the boli, distance between boli, size of boli, are closely related to the esophageal function, i.e., to the dynamics of the peristaltic movement of esophagus itself. As hereinbefore stated, the term "esophageal function" is herein taken to refer to the characteristics or dynamics of the peristaltic motion or waves provided by the esophagus during activity thereof, that is including swallowing and reflux, and thus the term "esophageal function parameter" relates to any suitable parameter that represents such motion. Thus, according to the present invention, the esophageal function parameters may be conveniently expressed as at least one of, and preferably all of the following: propagation direction, inter-boli time and space intervals, velocity and acceleration of peristaltic waves. Thus, in general, the direction and velocity of the boli correspond to the direction and velocity of the corresponding peristaltic waves, and the distance between boli is related to the wavelength between consecutive peristaltic waves.

The method of the present invention for evaluating or monitoring esophageal function of a patient, may be applied to a patient when the patient is in the process of swallowing at least one food bolus via the esophagus, and comprises the following steps:

(g) acquiring ultrasonic image data of at least one bolus at a plurality of temporal intervals as said bolus passes through the esophagus;

(h) tracking said at least one bolus in said image data to identify esophagus and bolus image data corresponding to the bolus and to said esophagus in said image data;

(i) determining at least one esophagus function parameter from the said bolus and esophagus image data.

In other words, the method may be applied while a patient is in the regular process of swallowing food, and thus does not require a special bolus to be ingested for the purpose of the method. On the other hand, there may be occasion in which the method is applied to a patient in-between meals, and includes a pre-step of providing suitable food for the patient who may then swallow the same, and continue with steps (a) to (c) above. The necessity for a patient to swallow food in a normal manner, while being a condition that must exist so that the bolus may be subsequently monitored or analysed, is not necessarily provided in order to conduct the method, and may exist in any case whether the method is applied or not, simply because the patient needs to eat. This in fact demonstrates the non-invasive character of the method, since food is not considered an invasive substance, but rather part of the normal activity of the body. Nonetheless, for the method of the invention, certain foods are preferred, particularly if they provide improved contrast in ultrasonic imaging and also if they provide smoother bolus flow in the esophagus. Such foods are preferably of uniform consistency and are relatively opaque to ultrasonic radiation, and are preferably incompressible, typically liquid or semi-liquid. Such foods may include, for example, milk, milk formula, porridge and so on. The specific preferred type of food may differ with patients, according to age, symptoms and so on, for example. Optionally, a suitable contrast medium may be added to the food being ingested. Other types of food are also possible, and may include sonicated liquids, such as soda water for example, in which microcavitation in the liquid improves visualization of the image of the liquid bolus and provides better signal to noise ratio. Furthermore, the ultrasonic imaging techniques themselves are also non-invasive.

The effects of added medication on the esophageal function may also be investigated, by performing the invention, first with "neutral" food, such as milk and so on, and then with added medication. Similarly, the effect of certain foodstuffs on esophageal function may be investigated by comparing the esophageal function obtained with such foodstuffs with respect to a "datum" food such as milk, for example.

Also, the effect of the position of the patient on esophageal function may be determined by evaluating the esophageal function when the patient is lying down, sitting or in any other position, and this may be carried out in conjunction with, or independent of, the investigation of the effect of added medication.

Typically, a patient swallows food in the normal manner, and typically sufficient quantity of food such that at least one bolus, and preferably a series of boli, are passed through the esophagus. More preferably, the patient continues to swallow food boli until sufficient data in step (a) are collected.

Notwithstanding the above, it is possible to also conduct the method of the present invention other than at mealtimes, when the patient would not normally be eating in which case the patient swallows at least one bolus of food, which can then form the basis of the imaging and analysis of the steps (a) to (c).

According to the first embodiment of the present invention, in step (a), the passage of the boli through the esophagus is recorded by means of the ultrasonic imaging system. Preferably, the ultrasonic imaging system (10) (or ultrasonic imaging means) comprises a suitable ultrasonic transducer (30) that is aligned as well as possible with the axis of the esophagus. As will become clearer hereinafter, such alignment does not require to be particularly accurate, though there are advantages if this is so. As the boli pass through the esophagus, image data of the part of the body covered by the transducer is recorded at relatively small time intervals ($t_i$), typically every 30 msec or less. At each time interval, the image data contains spatial information of bolus within the esophagus. Further, the system according to the present invention also enables dynamic measurements including velocity and acceleration to be performed in parallel to the imaging, and thus, at each time interval, the image data contains spatial and dynamic information relating to the bolus within the esophagus, corresponding to a given temporal value. Any suitable technique, method and/or apparatus that provides such dynamic data may be used. In the first embodiment, a Doppler-based technique is used, typically comprising the acquisition of pulsed Doppler velocity data, typically procured using a suitable tissue velocity imaging technique, advantageously a suitable colour-coded velocity imaging technique, and such techniques are well known. Thus, in step (a), image data including spatial and dynamic data is acquired at discrete time intervals of 30 msec or less, and this data is stored in the analysis means (20) of the system (100).

In step (c), the data acquired in (a) is manipulated and analysed to determine the esophageal function of the esophagus being studied, and this preferably takes the form of calculating certain standardized esophageal function parameters, including:—

Net direction of travel of the boli, i.e. antegrade or retrograde or non-propulsive.

Average velocity of boli within the esophagus. This refers to both the average velocity of any particular bolus during passage thereof in the esophagus, and also the average velocity between a number of consecutive boli swallowed during one data acquisition session.

Average distance and/or time interval between consecutive boli swallowed during one data acquisition session.

Acceleration of antegrade and retrograde propagation of the boli. This is useful for assessment of esophageal strictures and in evaluation of reflux.

Analysis of the data acquired in step (a), in steps (b) and (c), may be performed off-line, that is after data acquisition has been completed. Alternatively, step (c) may be performed "on-line". In "on-line" mode, analysis of some esophageal parameters is conducted in real time, for example, the direction and velocity of boli passing a particular point in the esophagus.

The off-line mode has the advantage that the operator may interact as desired with the stored raw data, and is thus not restricted to any particular automated analysis method. On the other hand, on-line analysis enables the operator to immediately review the esophageal parameters obtained, and thus can more easily decide if and how to change the test parameters to obtain the best results. Preferably, the method is used in on-line mode, but the raw data is stored to enable post-procedure off-line analysis as well, if desired to do so by the operator.

Figure 2:
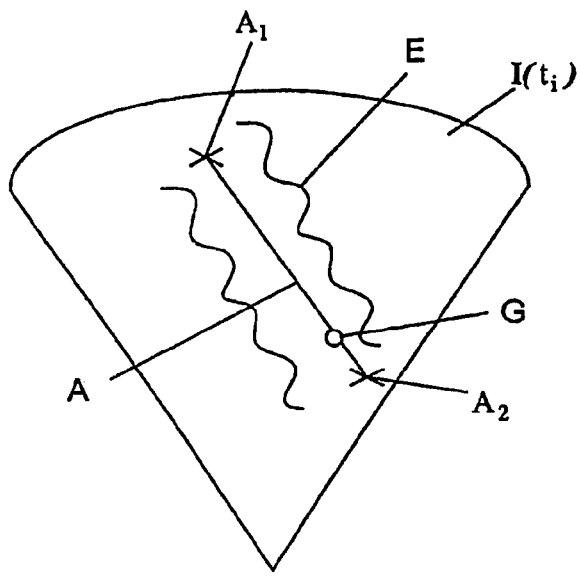
FIG. 2 schematically illustrates typical image data obtained at any particular time interval using the system in FIG. 1.
Figure 3:
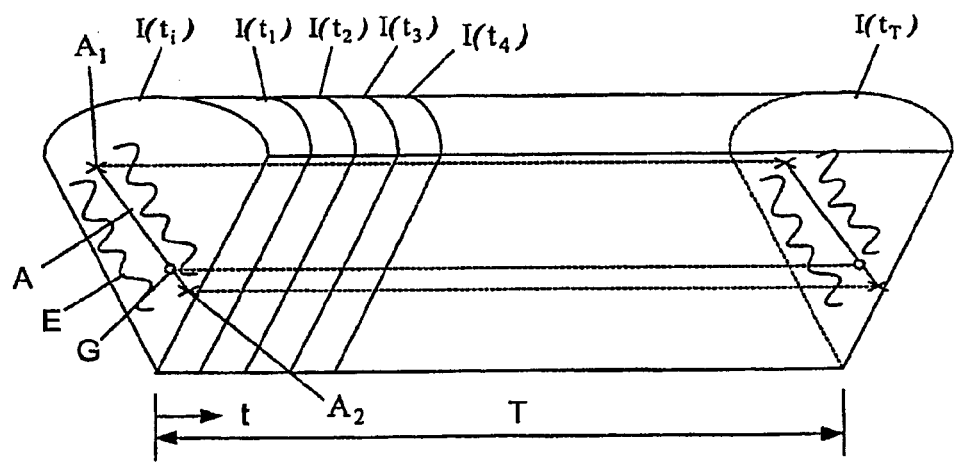
FIG. 3 schematically illustrates a series of consecutive sets of image data obtained within a time period.
Figure 4:
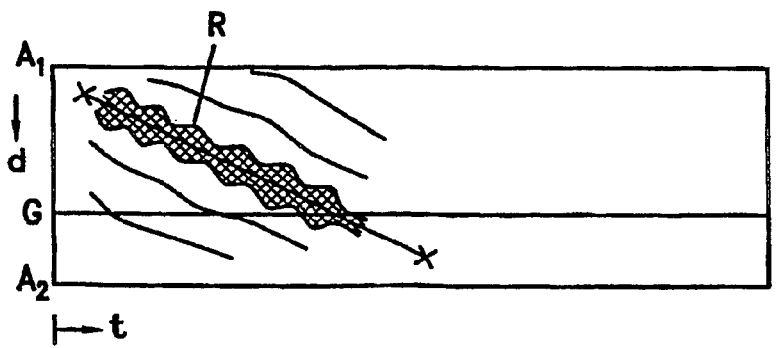
FIG. 4 schematically illustrates a slice of data taken from FIG. 3 corresponding to axis A in FIGS. 1 and 2.

Step (b), off-line, generally takes the following form. Referring to FIG. 2, the image data ($I(t_i)$) (also referred to herein as a frame of data) taken in step (a) for a series of consecutive time intervals, i.e. along the time domain, is visually inspected by the operator, the esophagus (E) is identified is then generally identified by tracking and determining the trajectories of the boli. The axis (A) of the esophagus is marked on one of the image data ($I(t_i)$), typically by marking two end points (A1) and (A2) by means of a cursor (typically an M-mode cursor), and joining these points, and spatial location of the axis (A) with respect to the image data (D) is input into the analysis system (20). Typically, the preferred data for calculating the esophageal function parameters will lie along this axis, and the one-dimensional image or scanline obtained is typically termed an A-line. Referring to FIG. 3, the analysis unit similarly marks all the consecutive data images for the complete time period (T) being investigated by the operator. Thus, the A-line is in the same position relative to each of image data ($I(t_i)$). Preferably, however, global movement of the esophagus is determined, and the A-line is appropriately compensated for from image to image, in a similar manner to that described below for the second embodiment, mutatis mutandis. The data in each of the consecutive data images ($I(t_0)$), ($I(t_1)$), ($I(t_2)$), ($I(t_3)$), ($I(t_4)$) . . . ($I(t_n)$), along the axis (A) can then be extracted and displayed side by side to provide an M-mode representation of the image data along the axis (A) with respect to time, as illustrated in FIG. 4. Thus, in this time-mode or M-mode display, a one-dimensional image, a single A-line, is repetitively scanned and displayed over time. Alternatively, it is also possible, and preferable, to provide an equivalent A-line for each image that is closer to the actual curved axis of the esophagus, in a similar manner to that described with respect to the second embodiment hereinbelow, and with particular reference to FIGS. 23 and 24, mutatis mutandis, to provide a Curved Anatomical M-Mode (CAMM) representation of the image data with respect to time.

According to the first embodiment of the present invention, there are at least two different approaches to the analysis of the image data in step (c): focusing on the dynamics of a bolus as it traverses the esophagus, herein referred to as the "bolus analysis method"; focusing on a location or region of interest in the esophagus, herein referred to as the "regional analysis method".

In the "bolus analysis method", when dynamic data, obtained by the Doppler measurements, is superimposed onto the image data in FIG. 4, the passage of a bolus is identified by the high velocity areas (R) therein. Accordingly, the slope of high velocity areas in FIG. 4, that is the distance covered by the bolus (vertical axis) over the time taken (horizontal axis) can be used to provide the average velocity of the bolus within the esophagus. Typically, and for ease of use, the Doppler data can be displayed as colours, for example with antegrade velocities in increasing magnitude shown red to yellow, and retrograde velocities shown in increasing magnitude shown blue to green. Any suitable colour scheme may be used.

This type of analysis provides information of how the esophagus as a whole is operating, since it follows the dynamics of one or more boli from the throat to the stomach, and thus esophageal parameters of interest are average bolus velocity (or transit time to stomach), smoothness of propagation of bolus through esophagus among others.

Figure 5:
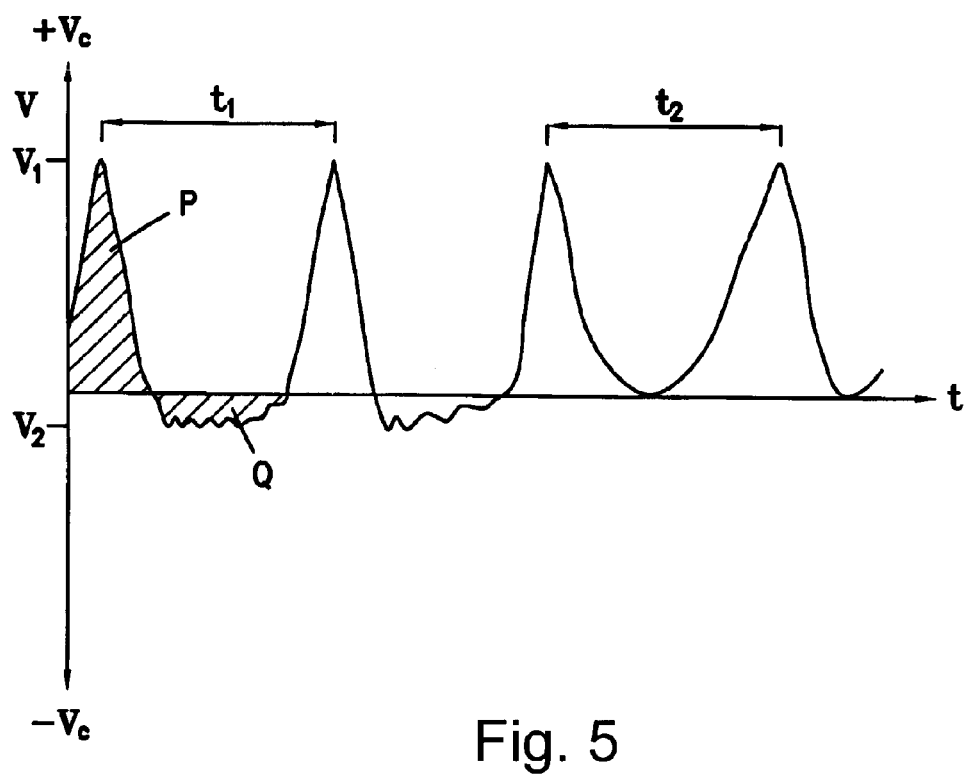
FIG. 5 schematically illustrates a typical velocity-time distribution obtained at point (G) in FIG. 2 during antegrade mode of the esophagus.

Other esophageal parameters of interest can also be obtained from the raw data represented in FIG. 4. For example, at a particular point in the esophagus, marked (G) in FIG. 2, for example, the Doppler information corresponding to this point may be analysed for each of the consecutive frames or sets of data represented in FIG. 3. This is the basis of the "regional analysis method". The Doppler analysis provides the measured velocity at region or point (G) with respect to time, and thus provides a picture of the velocity (V) vs. time (t) at (G), and thus the general behaviour of consecutive boli passing point (G). Practically, the colour of one or a group of pixels at (G) represents the velocity measured at this point. Thus, referring to the right part of FIG. 5, a typical velocity (V) vs. time (t) relationship is represented, wherein the velocity at (G) peaks at a given value (V1) approximately every (t2) seconds. This relationship illustrates a typical healthy antegrade esophageal function, in which successive boli pass point (G) in an antegrade direction. The left part of FIG. 5 represents a less optimal esophageal process, in which the high velocity peaks are intercalated with negative velocity troughs of velocity (V2), and this may be interpreted as follows. A first bolus passes point (G) at velocity (V1), then part of the bolus spasmodically reverses direction to retrograde at low velocity (V2), and is then followed by this part and the next bolus passing point (G) at velocity (V1), and so on.

This type of analysis, focusing on a point or region in the esophagus, rather than on a specific bolus, provides general information regarding the mode in which the esophagus is operating—antegrade, retrograde or non-propulsive. This form of analysis can also provide other information. For example, in the type of velocity-time distribution illustrated in FIG. 5, each high velocity peak represents a bolus passing through point (G) in the esophagus. By integrating the area in the distribution between these peaks, marked for example as (P) and (Q) in the left part of FIG. 5, a measure of the distance between boli can be approximated, and thus provides a measure of the wavelength or the inter-wave distance of the peristaltic waves at (G). Similar analyses may be conducted at other points in the esophagus to obtain a broader picture of the esophageal function.

The analysis of step (d) can be performed on-line. In particular, the regional analysis method can be performed on-line, since velocity data can be obtained directly concerning any region or point of interest in the esophagus. Essentially, the cursor in the analysis unit (20) is used to identify a location (G) in an image (I(t$_i$)), and subsequently, all velocity data relevant to this point (G) is displayed in real time as the operator is using obtaining image data. This way, the operator can immediately see whether the esophagus is operating in antegrade mode, retrograde mode, or if in fact in non-propulsive mode. Furthermore, by integrating the velocity/time relationship, the mode of propagation of the esophagus can be determined to be antegrade mode, retrograde mode and non-propulsive modes, according to whether the said integral is substantially positive, negative or zero, respectively.

EXAMPLE I

The following example is provided merely to illustrate the invention according to the first embodiment, and is not intended to limit the scope of the invention in any manner. While the method of the invention is applicable to any patient of any age, it will be described in this example with reference to a specific clinical study on newborn infants.

Disturbance in deglutition and reflux are extremely frequent in the first year of life of a child. Moreover, many recurrent respiratory infections, asthma and other respiratory diseases have been associated with recurrent gastrointestinal reflux. Therefore there has been considerable interest in developing means of evaluating the esophageal function in young children that overcome the difficulties inherent in the prior art methods described hereinabove, especially as those difficulties would effect the testing of young patients. In order to establish if the method of the present invention satisfies this interest, a study was carried out on a group of 34 newborn babies aged 12 to 48 hours.

The babies were studied while drinking a 30 cc formula substitute meal. The meal was given at least 3 hours after the preceding feeding, after ascertaining with ultrasound that the stomach was empty. The babies were fed while lying in a cot at 30° anti-Trendelenburg angle.

The method of the invention was performed using a GE Vingmed System Five unit using a 5 MHz probe at 7.5 MHz imaging and a frame rate ranging from 45-200 Hz. This machine has the unique capability of storing raw data for further off-line analysis, a feature which facilitates and shortens the acquisition time since no measurement needs to be made on-line. The images were obtained using a modified subxiphoid short-axis echocardiographic view. Attention was paid to visualize the esophagus long axis adjacent to the posterior wall of the left atrium down to the lower esophageal sphincter and the upper stomach as can be seen in the photograph in FIG. 6.

In addition to conventional M-mode and Doppler modalities, the unit used allows a unique application called the "anatomical M-mode" (AMM). AMM allows off-line drawing of an M-mode line in any desired axis on the previously stored raw data, regardless of the position of the transducer. In other words, this feature allows orientation of the M-mode to the anatomy instead of to the transducer. This is particularly important for the method of the invention since it is never possible to align the long axis of the esophagus with the transducer position. Both M-mode recording and Doppler interrogation of the bolus were performed off-line using the previously recorded raw data. All of the qualitative and quantitative analyses were performed with the use of the Echo-PAC™ software provided with the unit.

All of the required data were recorded twice, first at the beginning of the meal, the "early phase", and then at the end of the meal, the "late phase". Five cine-loops were recorded during each feed. Each cine-loop lasted 700-3000 msec (median 2000) which typically included 1-3 peristaltic waves. Data for each wave in every cine-loop were averaged and multiple recorded cine-loops were further averaged. The final data were computed from 5-15 measurements for each type of wave (antegrade, retrograde) and for each method of analysis (M-mode, pulsed Doppler). Thus, two hundred and thirty four measurements were obtained during 45 feeds of the 34 infants included in the study.

Figure 6:
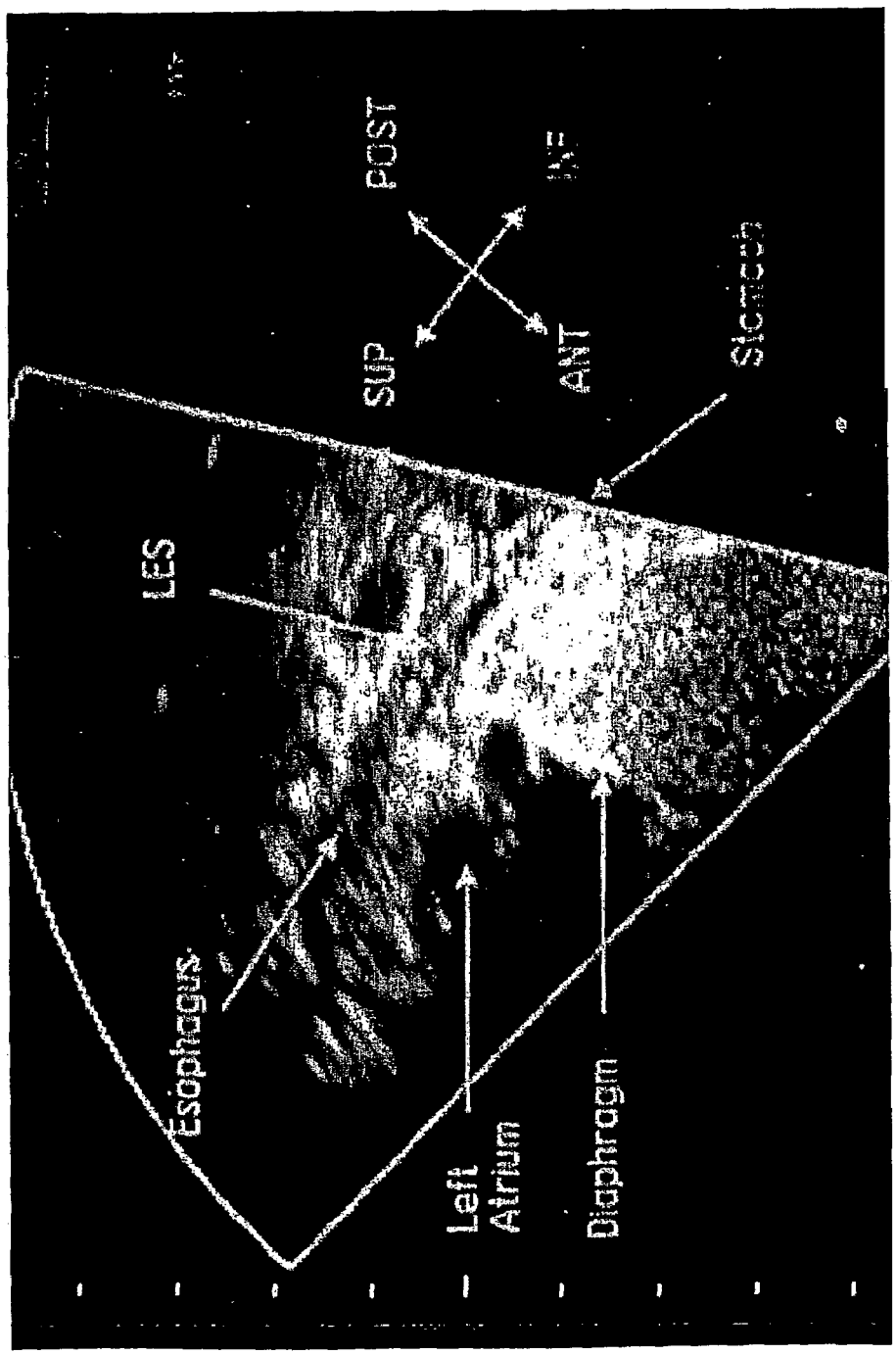
FIG. 6 is a photograph showing conventional (gray scale) 2D imaging of the bolus within the esophagus.

FIG. 6 is a photograph showing conventional (gray scale) 2D imaging of the bolus within the esophagus. The propagation of the bolus was inspected down to the lower-esophageal sphincter (LES) as it entered the cardia of the stomach. The distance between consecutive ticks on the vertical scale on the left of the photograph indicates 1 cm. The recognition of the bolus within the esophagus enabled the location of the exact axis and sampling of the velocity of the bolus from the acquired raw velocity data.

Adequate images, similar to those of FIG. 6, were obtained for all the babies using the modified subxiphoid "short-axis" echocardiographic view. In the data, 5 to 9 cm of the esophagus from the LES up to the upper esophagus is visible, i.e. ⅔ to 9/10 of normal length [5] was imaged. On-line data acquisitions lasted 2-10 minutes, according to the length of the feed.

On the right of the photograph the arrows show the standard directions for orientation, where: SUP=superior, INF=inferior, ANT=anterior, and POST=posterior.

Figure 7A:
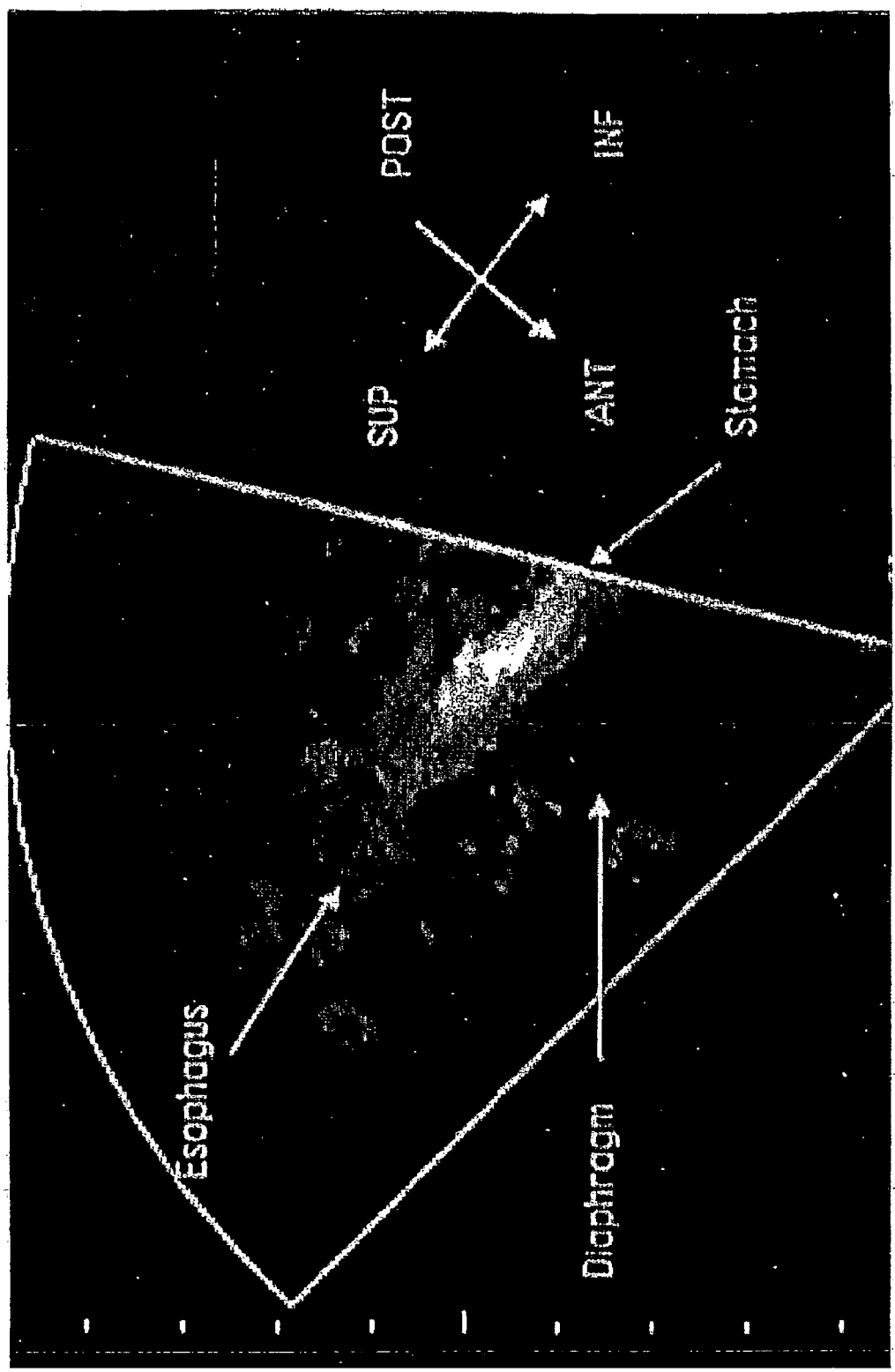
FIG. 7A is the same picture as in FIG. 6 incorporating Doppler velocity data (color encoded tissue velocity imaging (TVI) originally in colour but shown herein in shades of gray.
Figure 7B:
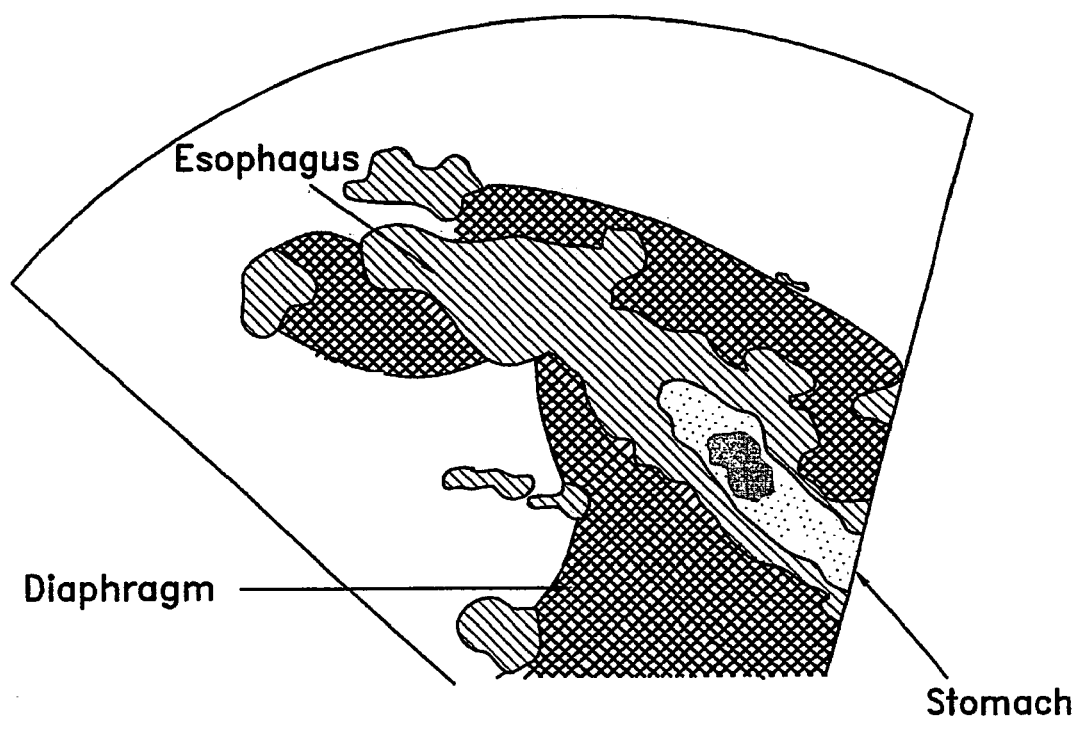
FIG. 7B schematically illustrates the different colour regions in FIG. 7A.

FIG. 7A corresponds to the image of FIG. 6 after switching to color encoded tissue velocity imaging (TVI). However, since the colour image is presented in FIG. 7A in black-and-white, FIG. 7B has been provided to clarify the coloured areas of FIG. 7A. With this color encoding of velocities, antegrade propagation (toward stomach) is shown in the colors red to yellow and retrograde motion of bolus (toward mouth) is shown in the colors blue to green. Using TVI, the direction and velocity of the propagation are readily assessed.

Figure 8A:
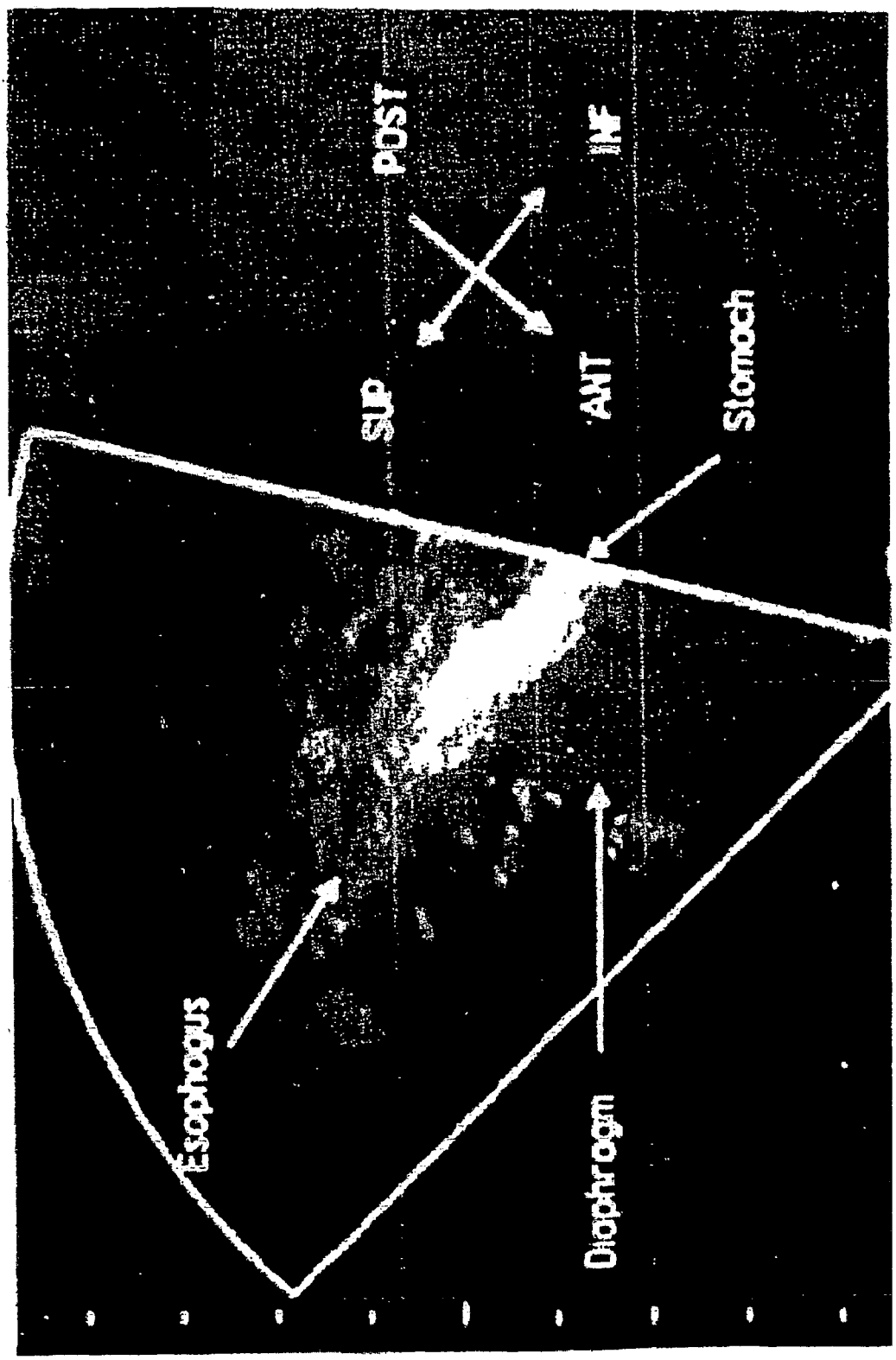
FIG. 8A is a photograph showing the display in the AMM, and FIG. 8B schematically illustrates the different colour regions in FIG. 8A.

FIG. 8A is a photograph showing the display in the AMM. In the upper panel of the figure, the anatomical M-mode cursor is shown aligned along the esophageal long axis. However, since the colour image is presented in FIG. 8A in black-and-white, FIG. 8B has been provided to clarify the coloured areas of FIG. 3A. The lower panel shows the AMM display of the bolus propagation. On the vertical axis is the distance (cm) in the esophagus from the pharynx to the stomach. On the horizontal axis is shown the time (sec).

Figure 8B:
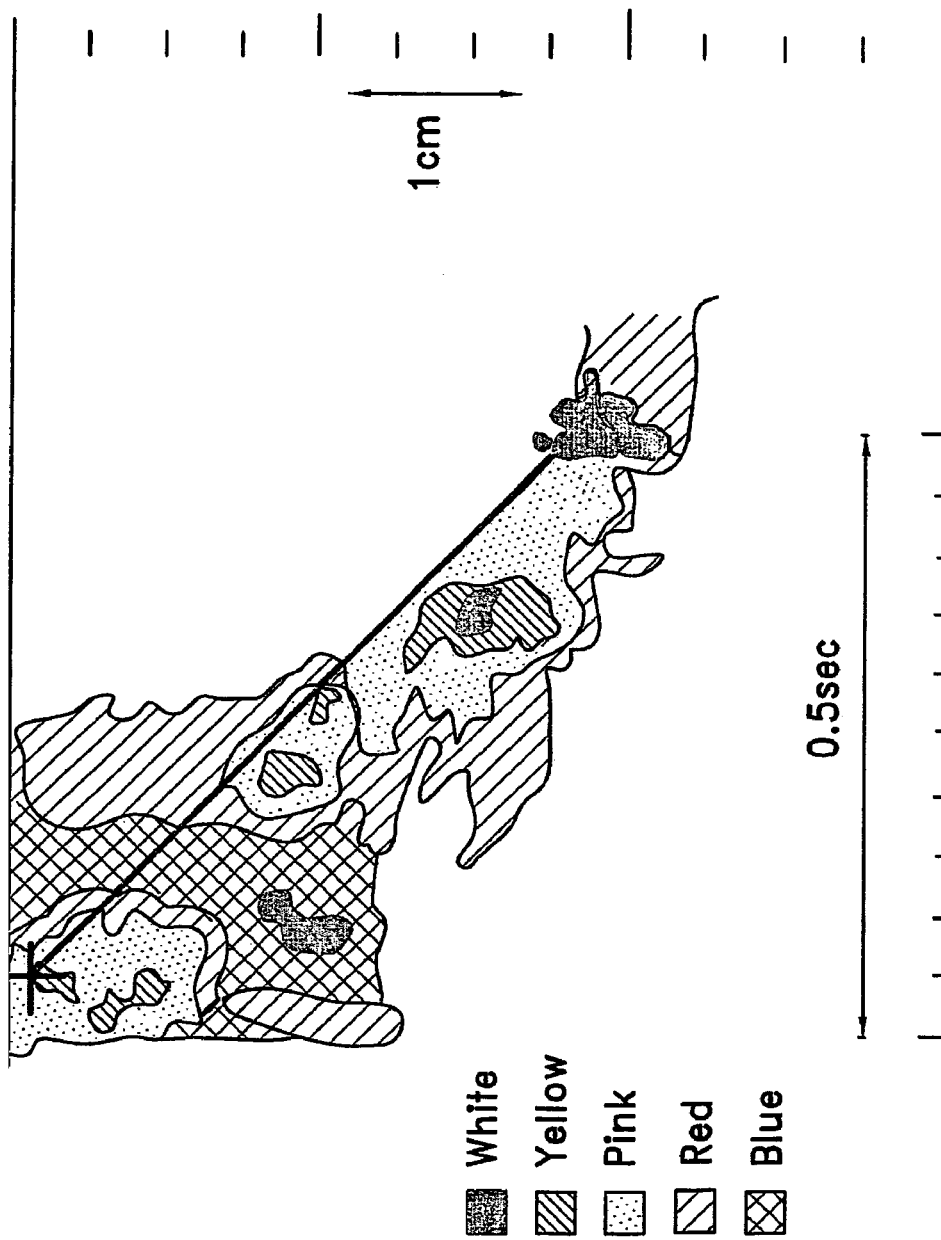

AMM was first displayed with grayscale and then using color-encoded TVI-M mode. In FIG. 8A and FIG. 8B, the slope velocity of the antegrade propagation is digitized along the interface between the yellow color-encoded M-mode and the background. In the figures short retrograde waves (blue) can be seen before the antegrade propagation (yellow).

Figure 9A:
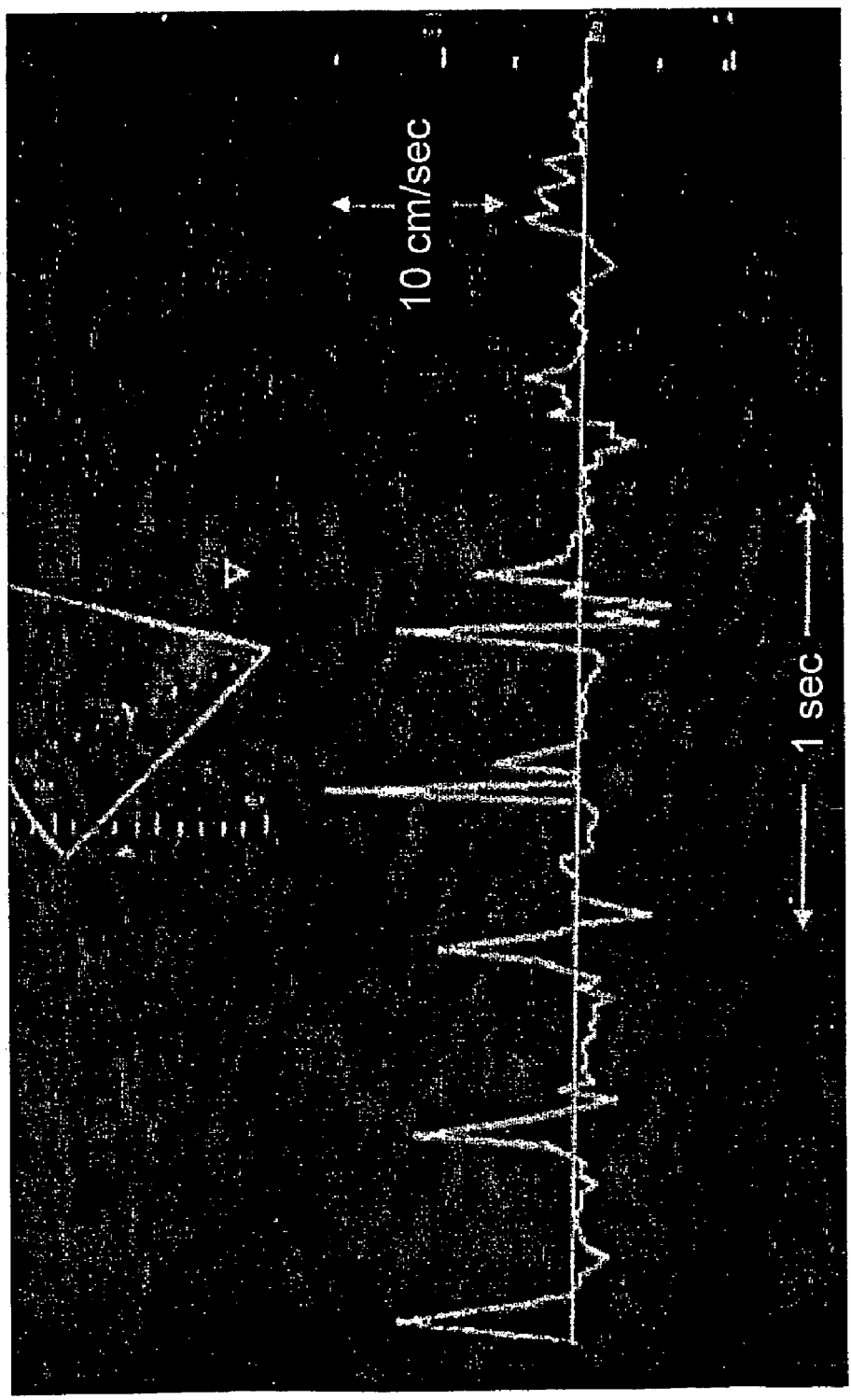
FIGS. 9A and 9B are photographs showing spectral pulsed Doppler velocity tracings.
Figure 9B:
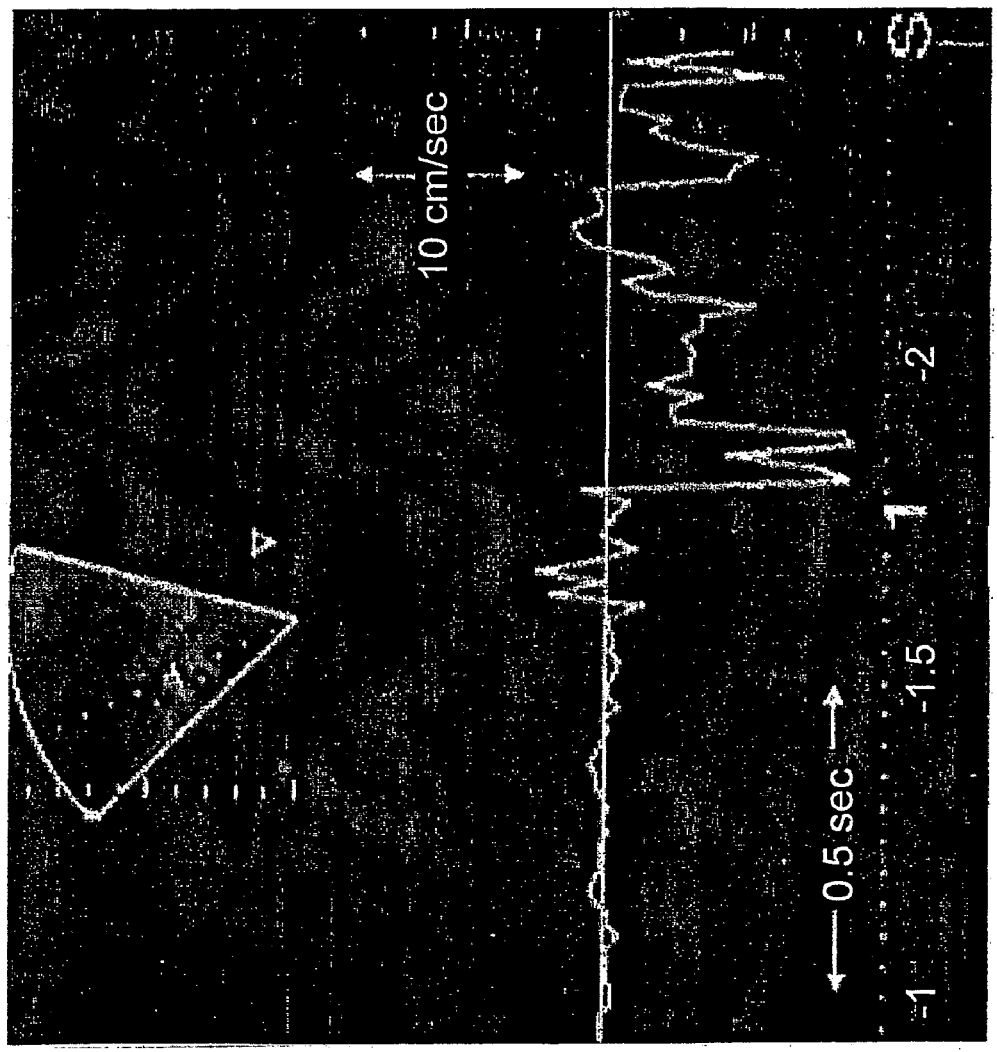

FIGS. 9A and 9B are photographs showing spectral pulsed Doppler velocity tracings. The tracings were obtained by sampling (2×2 pixels) of the propagating bolus from the raw data images at the same location on the esophagus. The upper panel in both figures shows that the cursor is positioned in the esophagus about 2 cm above the LES. In FIG. 9A, the lower panel shows a pulsed Doppler display of a series of boli in antegrade propagation. In other words, as a series of boli pass the point in the esophagus marked by the cursor, the velocities measured at this point are displayed in these figures. Thus excluding noise effects, FIG. 9A can be interpreted in the following manner: each bolus passes this point at a peak velocity of approximately 10 cm/sec, this is momentarily followed by a retrograde flow of part of the bolus, at low velocity, followed by this part and another bolus, with an inter-boli period in the range of 0.5 sec. In FIG. 9B the lower panel shows a pulsed Doppler display of a reflux. In this case, boli are flowing towards the throat, and the "retrograde" peak velocities are about 15 cm/sec. Although the wave-to wave time interval was relatively constant for antegrade propagation waves in FIG. 9A, such an interval could not be measured for the retrograde waves, which were mostly sporadic.

In this trial, using the method of the invention, the peristaltic waves of the neonate were observed and characterized. For antegrade propagation two types of peristaltic waves were identified: waves initiating high in the esophagus and waves initiating in the esophageal body. In addition, sequences of non-propulsive waves were also identified.

Figure 10:
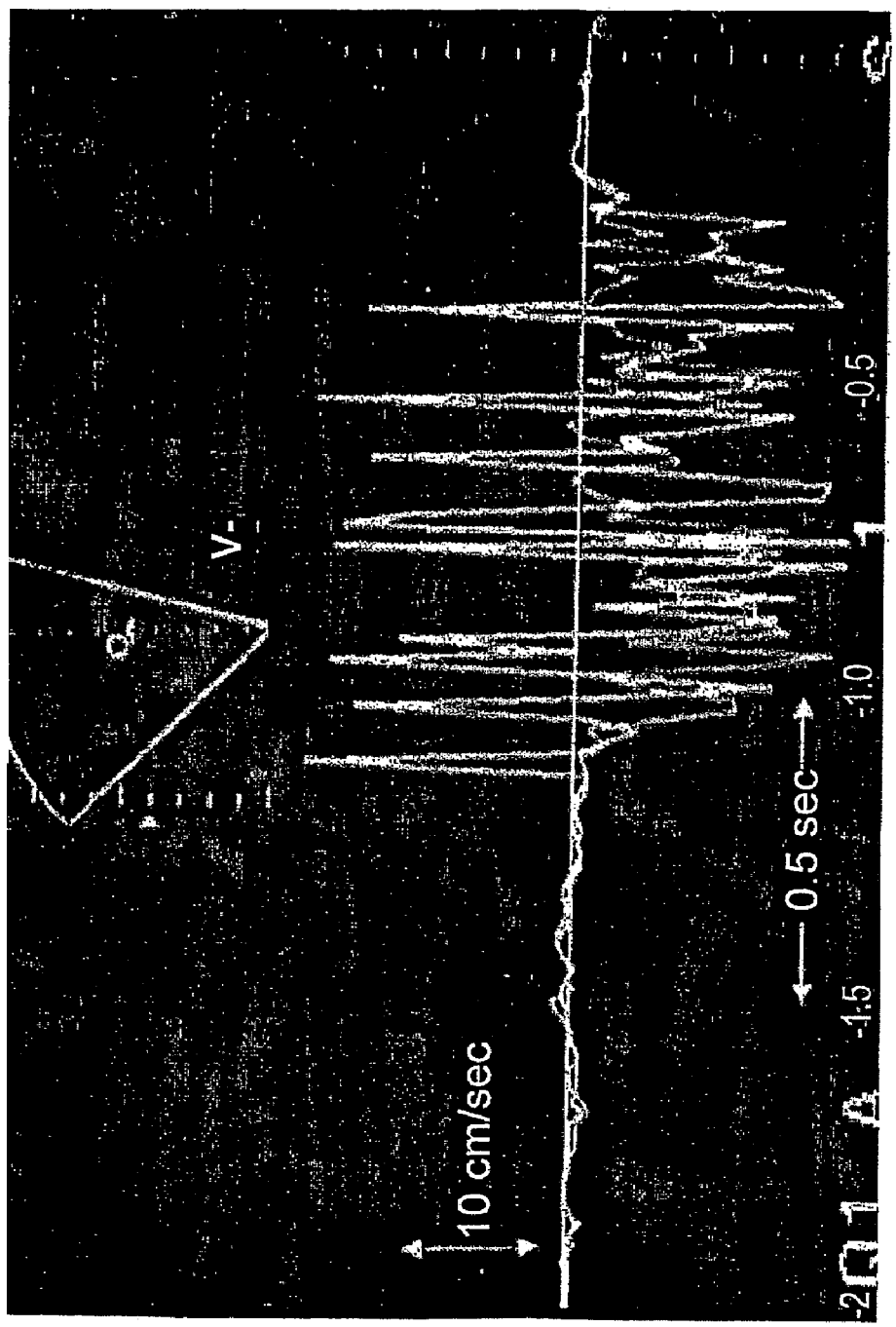
FIG. 10 is a photograph showing non-propulsive waves.

FIG. 10 is a photograph showing this last type of wave. The upper panel shows the position of the cursor in the esophagus about 2 cm above the LES with reference to which the velocities of boli passing therethrough were monitored. The lower panel shows pulsed Doppler display of a series of bi-directional fast motions of the boli with little effective propagation. In other words, the food boli were effectively oscillating within the esophagus, but without actually net movement towards the stomach or the throat. The net propulsive effect of these waves was negligible although high velocities (up to 16 cm/sec) were associated with both antegrade and retrograde motions.

For retrograde propagation two types of waves were identified. The first type is a retrograde propagation initiating in the lower esophagus. This type is shown in FIG. 9B. The waves tend to be of short period, and, are immediately followed by a fast antegrade boli swiftly moving the fluid back toward the stomach. The second, rarer, type of retrograde propagation initiates from a full stomach, with the lower esophageal sphincter widely open (0.8-1.3 cm). This occurs mainly at the later measurements, toward the end of the meal. These waves tended to be very swift (up to 100 cm/sec) and resulted frequently in regurgitated milk actually being spit out, as illustrated in FIG. 11A and FIG. 11B.

Figure 11A:
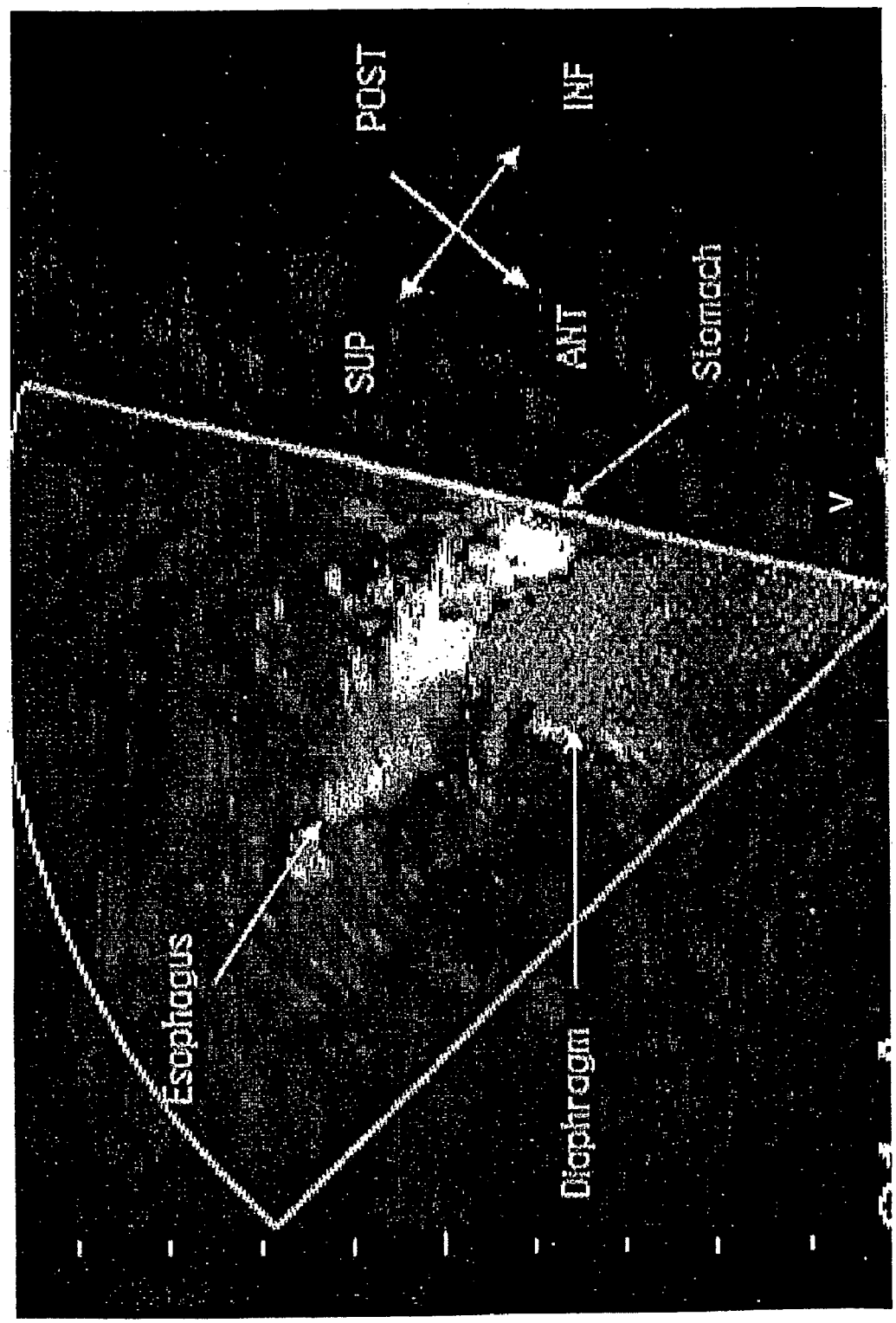
FIG. 11A is a photograph showing the two-dimensional imaging of a retrograde reflux from the stomach toward the esophagus.

FIG. 11A is a photograph showing the two-dimensional imaging of a retrograde reflux from the stomach toward the esophagus. However, since the colour image is presented in FIG. 11A in black-and-white, FIG. 11C has been provided to clarify the coloured areas of FIG. 11A, showing these coloured areas in different shading patterns. The scale and abbreviations are the same as in FIG. 6. With the use of TVI color encoding of velocities, the blue encoded retrograde flow originating in the stomach and passing through the widely open LES to the esophagus is clearly seen.

Figure 11B:
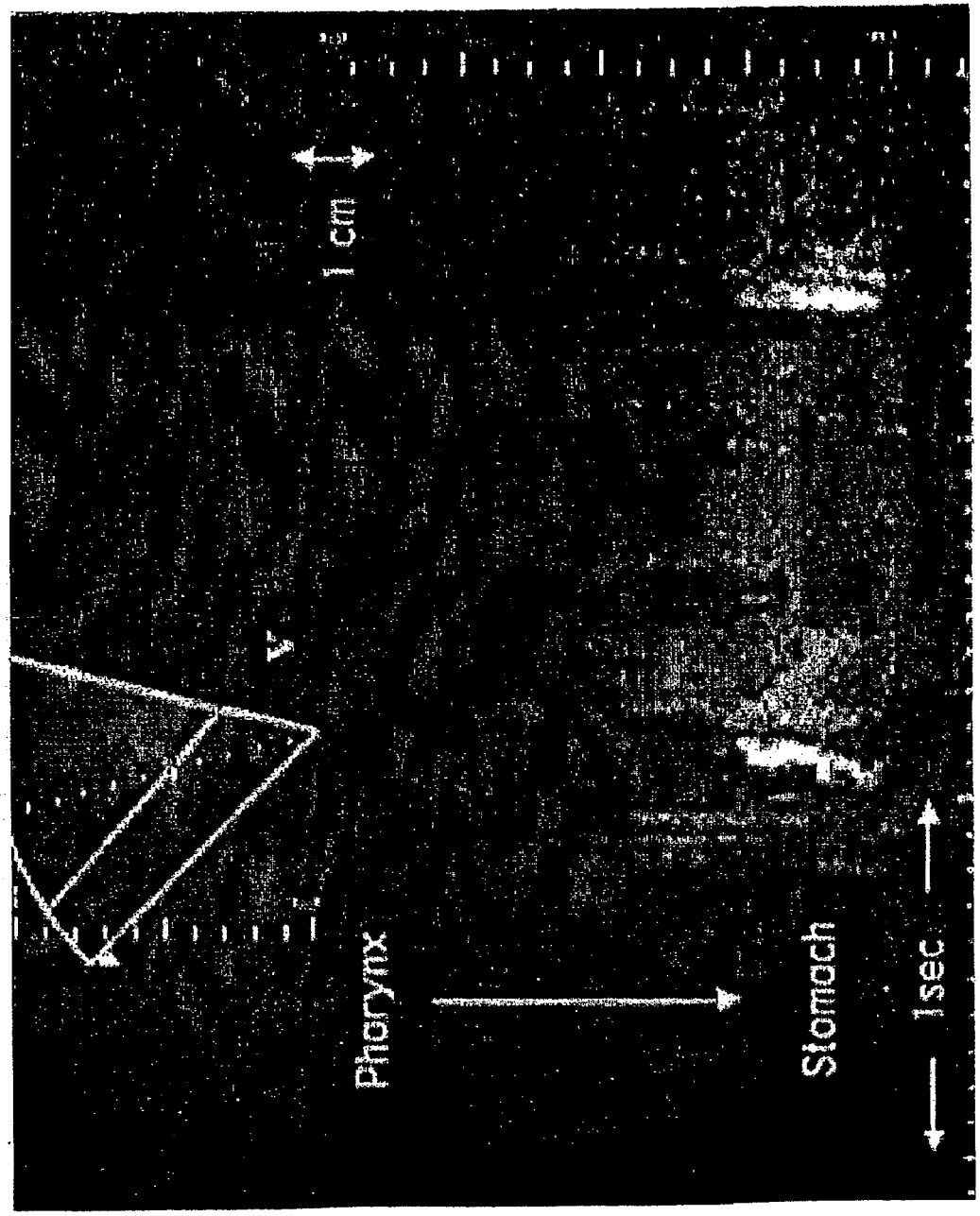
FIG. 11B is a photograph of an M-mode display of two waves of retrograde motion from the stomach toward the esophagus.
Figure 11C:
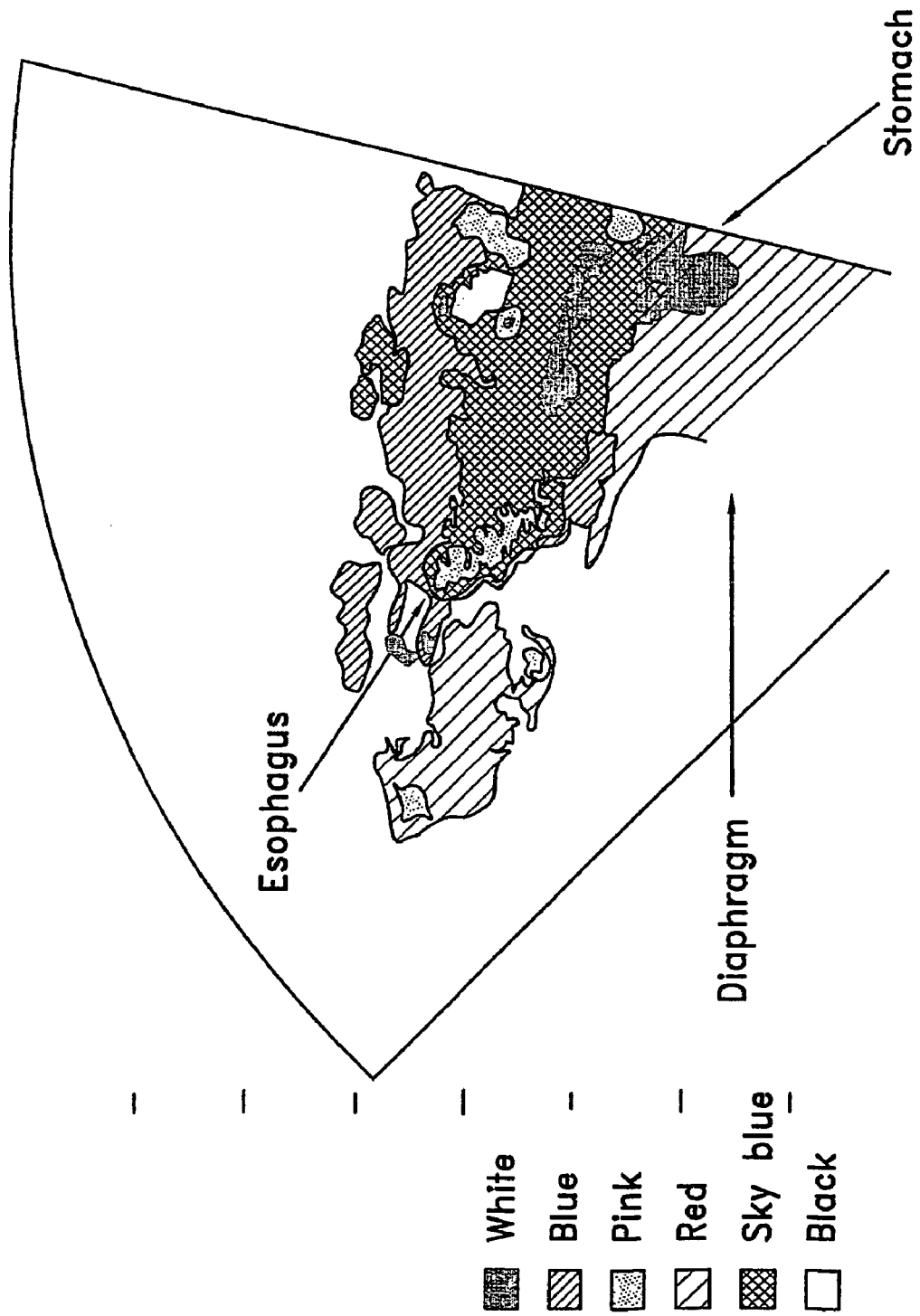
FIG. 11C schematically illustrates the different colour regions in FIG. 11A.
Figure 11D:
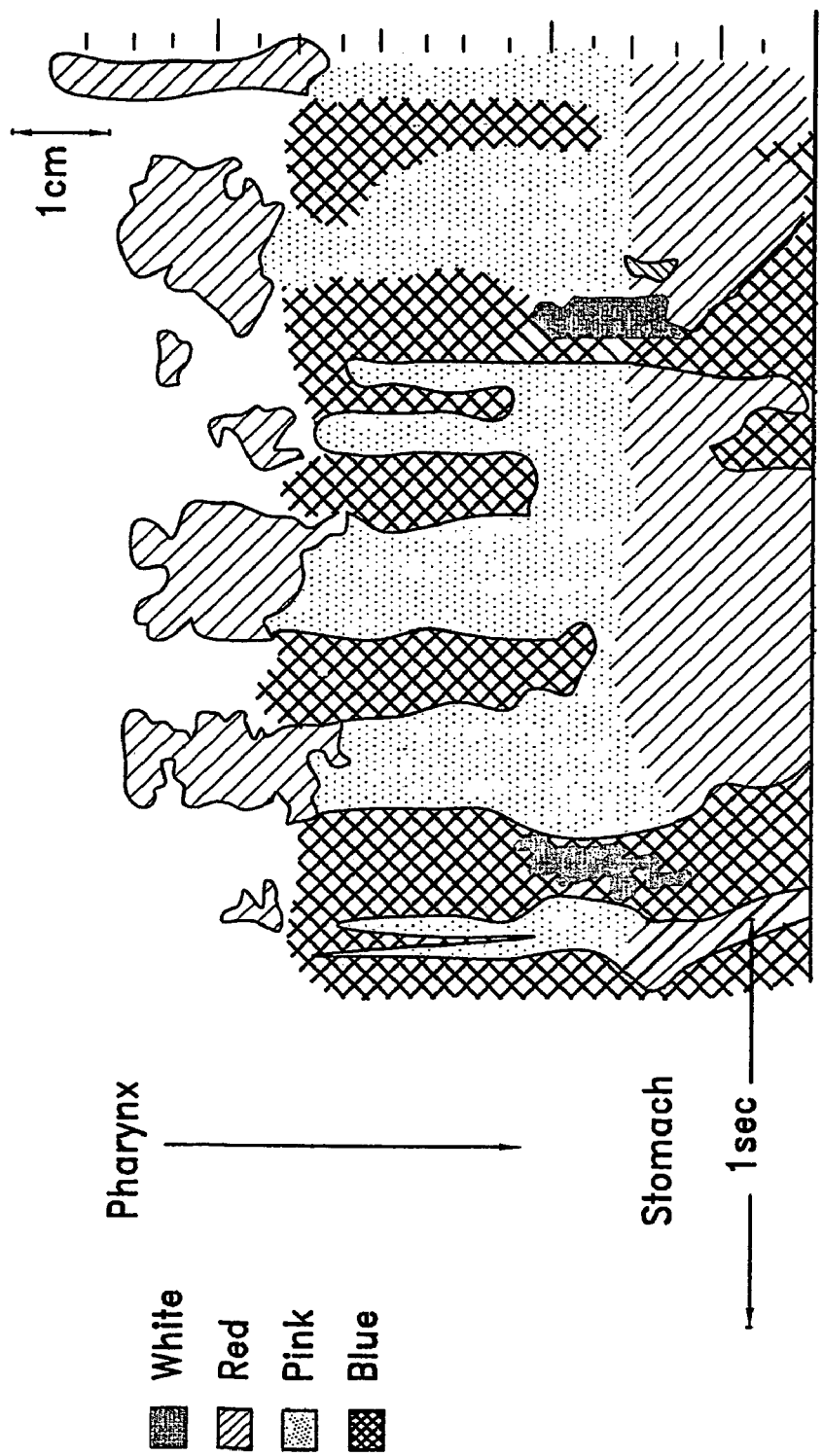
FIG. 11D schematically illustrates the different colour regions in FIG. 11B

FIG. 11B is a photograph of an M-mode display of two waves of retrograde motion from the stomach toward the esophagus. However, since the colour image is presented in FIG. 11B in black-and-white, FIG. 11D has been provided to clarify the coloured areas of FIG. 11B. The vertical axis shows distance (cm) in the esophagus and the horizontal axis time (sec). The slope velocity of the propagation is along the very steep interface between the blue-white color-encoded M-mode and the background and is in the order of magnitude of 100 cm/sec.

In addition to antegrade and retrograde propagation, a third form of bolus condition defined as a "suspended" bolus was observed. In this condition, there was no motion along the esophagus although it was full of milk. This type of "suspended" column of milk was observed at the late-phase feedings in 20% of the patients.

In order to analyze the quantitative results, various methods of statistical analysis were employed. Using software from Jandel Scientific (San Rafael, Calif., USA), descriptive statistics, one way analysis of variance, and Kruskal-Wallis one way analysis of variance on ranks were applied as appropriate. Pairwise multiple comparison procedures were performed using the Student-Newman-Keuls method in order to compare M-mode and Doppler data, and to compare retrograde velocities to antegrade propagation velocities. Early versus late phase boli data as well as antegrade versus retrograde velocities were also compared in all modes. A p value of 0.05 or less was considered significant.

In Table 1 are displayed the M-mode bolus velocity measurements calculated for antegrade and retrograde waves at early and late phases of the feedings. In Table 1 (and also in Table 2): A1=early antegrade waves, A2=late antegrade waves, R1=early retrograde waves, and R2=late retrograde waves and S.E.=standard error of estimates. These bolus velocity measurements were provided by performing AMM analysis of the image data, identifying the passage of the bolus in the distance-time AMM image (such as those of FIGS. 8A, 8B, 11B and 11D, for example) and marking a linear trajectory of the bolus therein, and calculating the velocity from the slope of the bolus trajectory.

TABLE 1

M-mode bolus velocity measurements (cm/sec)

| | A1 | A2 | R1 | R2 |
|---|---|---|---|---|
| Mean | 12.4 | 13.1 | 23.4 | 33.3 |
| S.E. | 0.9 | 2 | 4.5 | 13.6 |
| Median | 12 | 10 | 16.5 | 19 |
| Min. | 3 | 6 | 4 | 4 |
| Max. | 24 | 33.5 | 56 | 166 |
| Count | 29 | 17 | 13 | 11 |
| Confidence Level (95%) | 1.9 | 4.2 | 9.9 | 30.3 |

Figure 12:
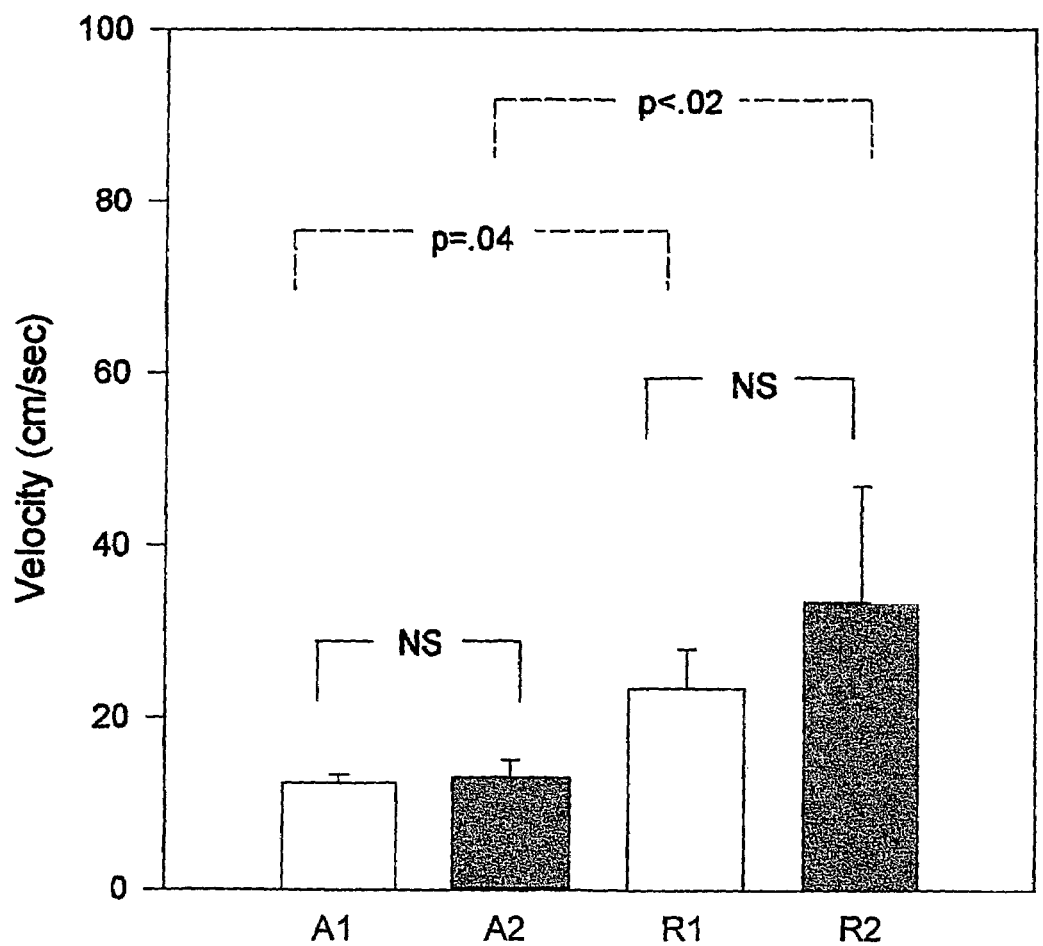
FIG. 12 shows in graphical form the results displayed in Table 1.

The results displayed in Table 1 are shown in graphical form in FIG. 12. In FIG. 12 the notation N.S. stands for "non-significant", and illustrates that while there the difference between the antegrade results at beginning and end of the meal are not significant statistically, there is a statistical significance in the difference between the antegrade and retrograde results, taken at the beginning of the meal ($p=0.4$) or at the end of the meal ($p<0.2$).

In Table 2 are displayed the Doppler measurements calculated for antegrade and retrograde waves at early and late phases of the feedings at about 2 cm above the LES.

TABLE 2

Pulsed-Doppler Velocity Measurements (cm/sec)

| | A1 | A2 | R1 | R2 |
|---|---|---|---|---|
| Mean | 10.42 | 12.51 | 14.33 | 15.83 |
| S.E | 0.78 | 1.25 | 2.23 | 1.34 |
| Median | 10 | 12.25 | 13.5 | 16.5 |
| Minimum | 5 | 6.5 | 7.33 | 11.5 |
| Maximum | 18 | 19.5 | 25 | 21.5 |
| Count | 19 | 12 | 7 | 7 |
| Confidence Level(95%) | 1.6 | 2.7 | 5.4 | 3.4 |

In Table 3 are displayed inter-boli intervals of antegrade propagation for M-mode and pulsed Doppler mode for a particular test. In the table, M=M-mode, P=pulsed Doppler mode, T=total boli, 1=early phase waves, and 2=late phase waves.

TABLE 3

Time Interval Between Boli (sec)

| | MT | M1 | M2 | PT | P1 | P2 |
|---|---|---|---|---|---|---|
| Mean | 0.86 | 0.70 | 0.90 | 0.82 | 0.84 | 1.04 |
| SE. | 0.19 | 0.134 | 0.21 | 0.06 | 0.11 | 0.19 |
| Median | 0.62 | 0.65 | 0.79 | 0.72 | 0.72 | 0.94 |
| Minimum | 0.24 | 0.31 | 0.11 | 0.21 | 0.33 | 0.37 |
| Maximum | 2.72 | 1.68 | 2 | 2 | 2 | 1.97 |
| Count | 14 | 10 | 8 | 52 | 16 | 9 |
| Confidence Level(95%) | 0.40 | 0.30 | 0.5 | 0.07 | 0.23 | 0.43 |

To summarize the results shown in these tables: antegrade velocities average $11.9\pm0.7$ cm/sec, the average velocities of the retrograde peristalsis is $23.6\pm2.8$ cm/sec, and the antegrade inter-boli interval mean is $860\pm190$ msec.

When comparing the different methods of quantification, no statistically significant difference is found between slope measurements in the M-mode versus the pulse mode either in the antegrade or in the retrograde boli, whether in the early or late classes.

Figure 13:
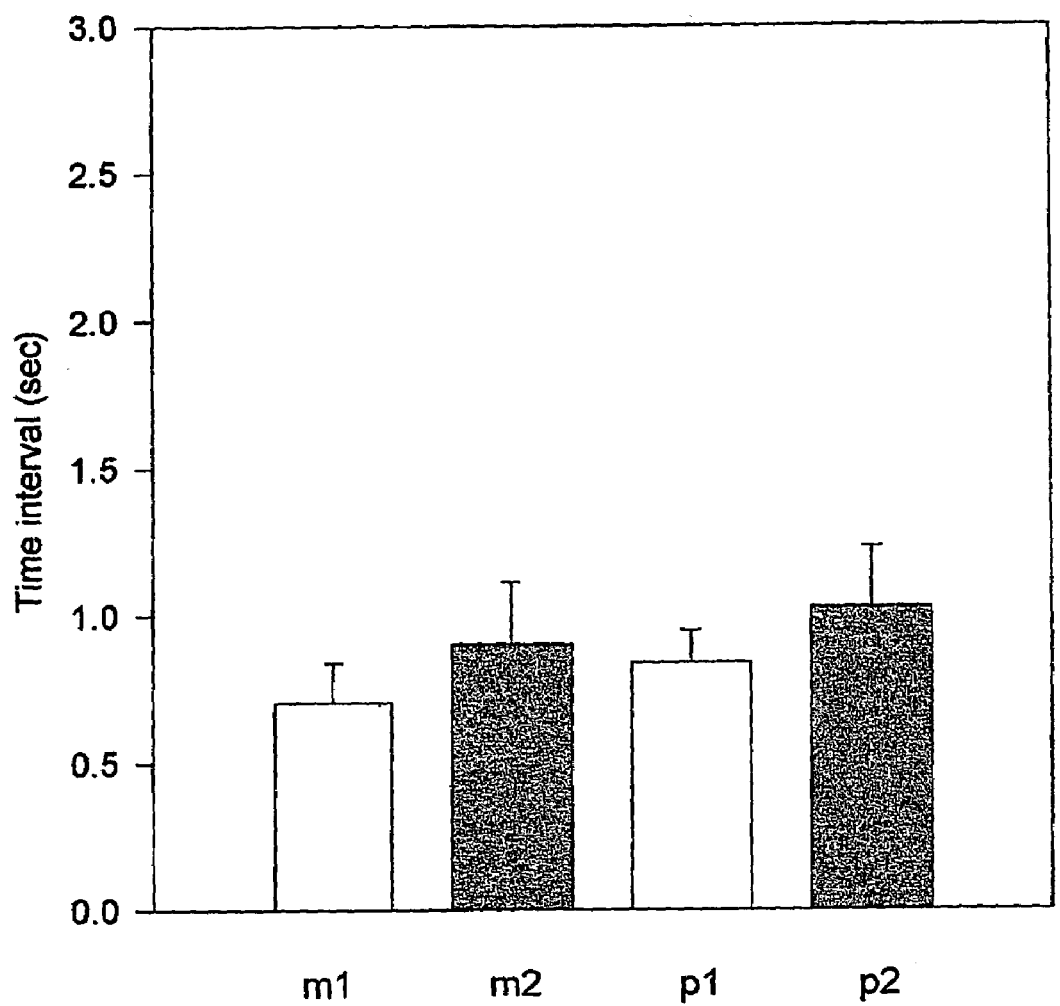
FIG. 13 graphically shows the comparisons of the m-mode with Doppler method using an unpaired t-test.

In FIG. 13 is graphically shown the comparisons of the m-mode with Doppler method using an unpaired t-test. For the antegrade early phase, the m-mode or Doppler method results are $12.4\pm0.9$ and $10.4\pm0.8$ cm/sec respectively with $p=0.13$. For the antegrade late phase the slopes of antegrade propagation at late phase when measured by m-mode or Doppler method are $13.1\pm2$ and $12.5\pm1.3$ cm/sec respectively with $p=0.82$.

Figure 14:
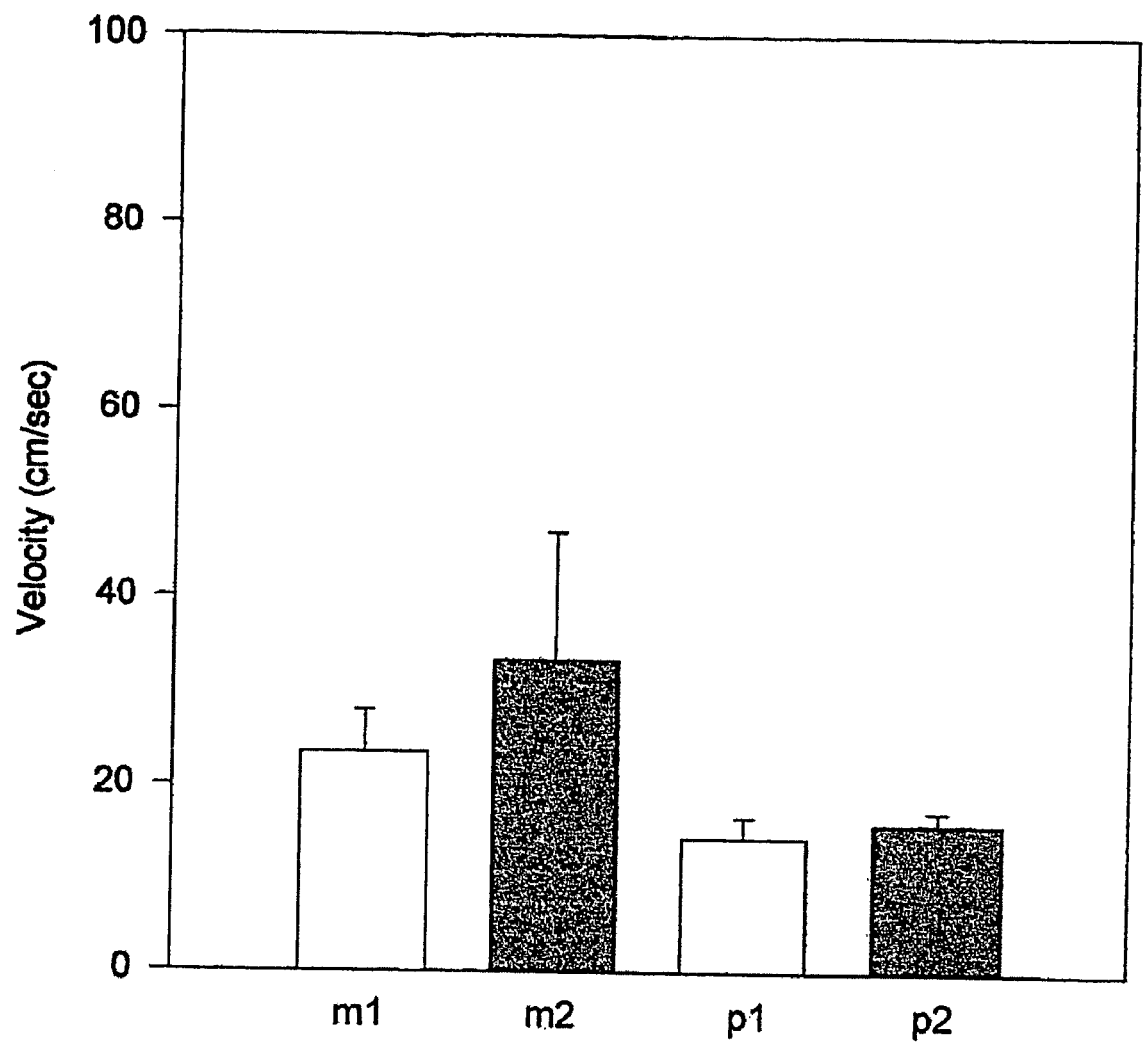
FIG. 14 graphically presents the results of the comparison of the m-mode versus pulsed Doppler method for retrograde velocity.

FIG. 14 graphically presents the results of the comparison of the m-mode versus pulsed Doppler method for retrograde velocity. The slope of retrograde propagation for the early phase did not differ significantly using the unpaired t-test when measured by m-mode or Doppler method. The results are $23.4\pm4.54$ cm/sec and $14.3\pm2.23$ respectively with $p=0.18$. For the retrograde late phase, using the Mann-Whitney Rank Sum Test (failed normality test), the m-mode and pulsed Doppler results do not differ significantly and are $19\pm12.8$ and $16.5\pm12.3$ for the median and 25% confidence level, respectively, with $p=0.28$.

Figure 15:
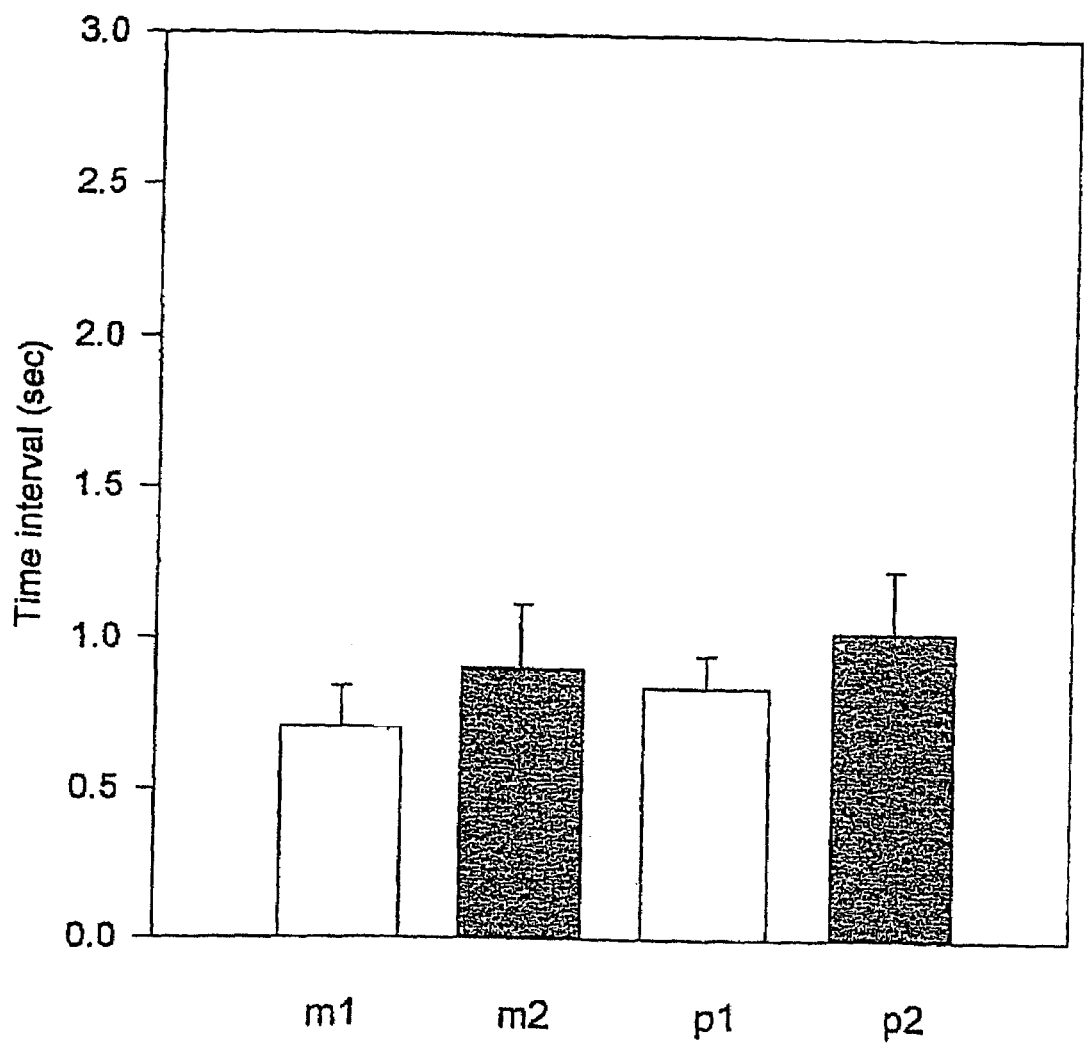
FIG. 15 graphically summarizes the results, displayed in Table 3, for the inter-wave intervals for antegrade waves.

FIG. 15 graphically summarizes the results, displayed in Table 3, for the inter-wave intervals for antegrade waves. The methods were compared using the unpaired t-test. The inter-wave interval did not differ significantly when measured by M-mode or Doppler method. The results being $0.71\pm0.13$ and $0.9\pm0.21$ sec respectively, for the early phase, with $p=0.42$. For the late phase the results, for the m-mode method, are $0.90\pm0.21$ sec and, for the Doppler method, $1.04\pm0.19$ sec with $p=0.64$.

From FIG. 15, it also can be seen that, again using the unpaired t-test, the results for the early phase and the late phase do not differ significantly for both methods. For the pulse-Doppler method the inter-wave intervals at early phase and late phase are $0.84\pm0.11$ and $1.04\pm0.19$ sec respectively with $p=0.34$. For the m-mode, the corresponding intervals are $0.71\pm0.13$ and $0.84\pm0.18$ sec with $p=0.44$.

Interobserver variability was evaluated by comparing results obtained by a pediatric resident without any prior experience in performing echocardiography or ultrasonography but nevertheless trained to perform Doppler esophagography tests (observer 1) to those obtained by an experienced echocardiographist (observer 2). The compared results were the antegrade bolus velocities sampling the raw data images. The two observers analyzed independently the raw data of 10 babies. The results of the comparison between M-mode antegrade late phase boli data are shown below, in Table 4. The mean antegrade propagation velocity for the experienced observer was 10.4±3.19-m/sec and for the inexperienced observer 12.7±1.96 m/sec. There was no statistically significant difference between the two observers (p=0.99).

Reproducibility was evaluated by repeating this comparison twice, with a one week interval between sampling. Intra observer variability was 18%.

TABLE 4

Early Phase Peristalsis

| | Observer | |
|---|---|---|
| | 1 | 2 |
| Mean cm/sec | 12.7 | 10.4 |
| SE | 1.96 | 3.19 |
| Median | 12.2 | 10 |
| Minimum | 6 | 1 |
| Maximum | 23 | 25 |
| Count | 10 | 10 |

The comparison of the measurements of two independent observers, as summarized in Table 4, shows not only that the measurements are repeatable, but also that previous experience in ultrasonography is not a prerequisite. Thus, this method of the invention can be performed by, pediatric gastroenterologists and neurologists, nurses and technicians in hospital or even in an outpatient clinic facility.

EXAMPLE II

A further study was carried out on a group of 15 newborn babies aged 2 hours to 14 days.

The babies were studied while drinking Remedia milk from a bottle, and image data acquired of the esophagus long axis from the subxyphoid approach.

The method of the invention was performed using a Vivid V GE echo system (WI, USA)_using a 5 MHz probe at 3.5 to 7.5 MHz imaging and a frame rate ranging from 50 to 200 Hz. The acquisition time was on average about 35 seconds (range 9-60 seconds) during feeding periods of 3-10 minutes, and 5-10 cineloops of 3-6 seconds duration were acquired for each baby. Raw scan line data was stored in 5.2 G MO disks. Analysis was performed off line using Echopac 6.3 software, with a time of analysis of about 20 seconds to 5 minutes per cineloop, the actual duration being related to the type and complexity of deglutition and quality of the recording.

All of the required data were recorded twice, first at the beginning of the meal, the "early phase", and then at the end of the meal, the "late phase".

As in Example I, bolus motion was easily detected, and the direction (antegrade vs. retrograde) was recognized immediately due to the colour enclosing of bolus velocity. The presence or absence of lower esophageal sphincter constriction was readily assessed.

The results obtained during this study may be summarized as follows.

Figure 16B:
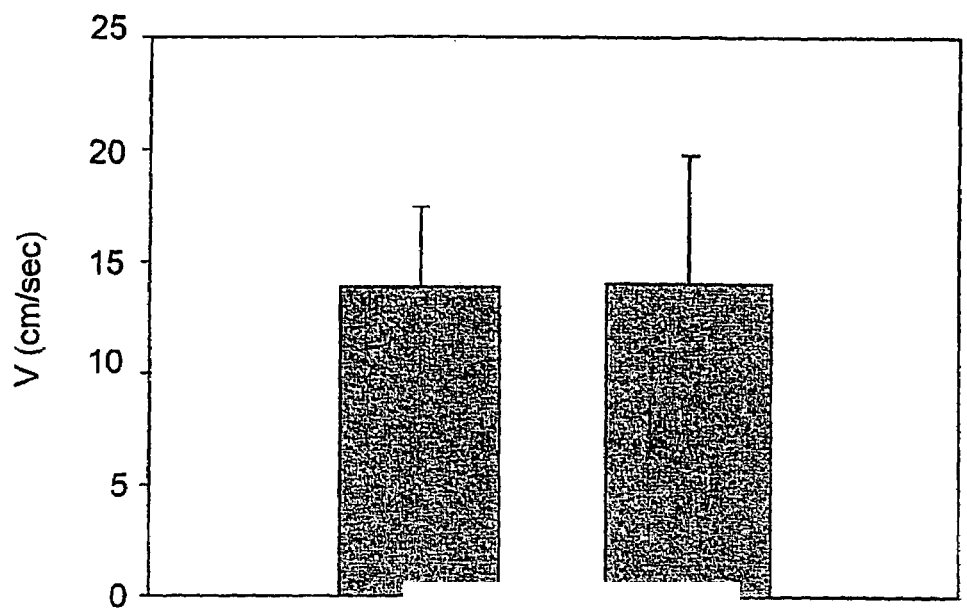
Figure 16B:
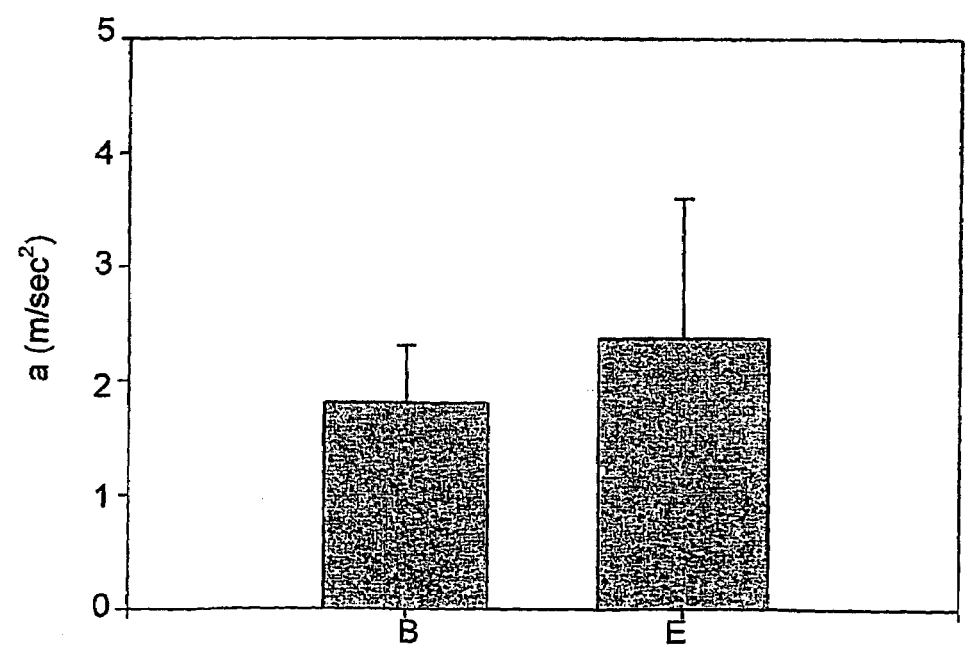

Referring to FIG. 16(a) and FIG. 16(b), antegrade velocity (V) averaged about 13.9±Standard Deviation (SD) 3.5 cm/sec at the beginning of the meal (B), and was not significantly different from the average antegrade velocity of 14.0±SD5.7 cm/sec at the end of the meal (E). Average acceleration (a) of the bolus at the beginning of the meal (B) was about 1.8±SD0.5 m/sec², and at the end of the meal (E) it was not very different at 2.4±SD1.2 m/sec².

Figure 17A:
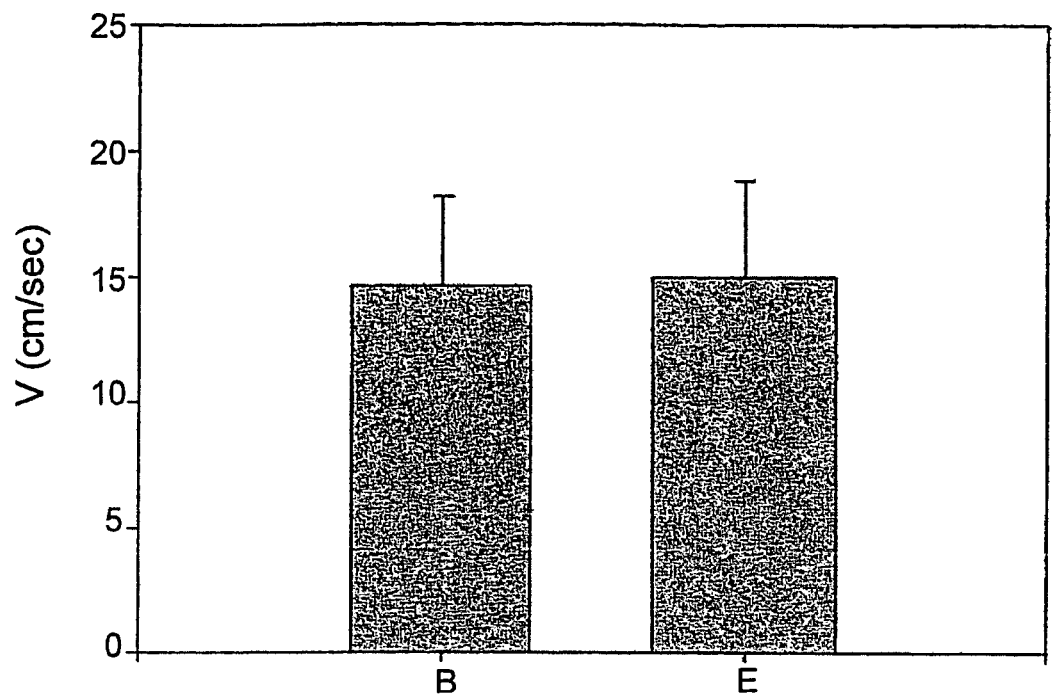
FIG. 17(a) and FIG. 17(b) graphically show the average velocities and the average interboli times, respectively, obtained at the beginning and end of the meal, in Example II.
Figure 17B:
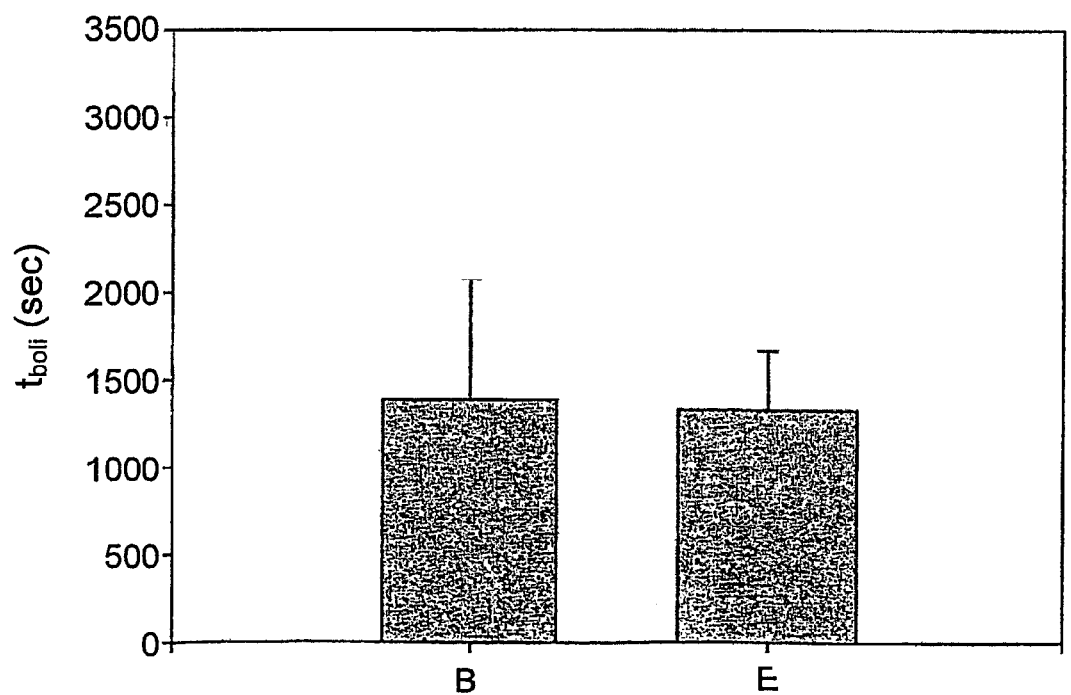

Referring to FIG. 17(a), retrograde velocity (V) averaged about 14.6±SD3.6 cm/sec at the beginning of the meal (B), and was not significantly different from the average retrograde velocity of 15.0±SD3.8 cm/sec at the end of the meal (E). Referring to FIG. 17(b), The average interboli time interval ($t_{boli}$) (related to the peristaltic period) of 1386±SD690 msecs at the beginning of the meal (B) was not significantly different from the average interboli time interval at the end (E) of the meal (1332±SD337 msecs).

Figure 18:
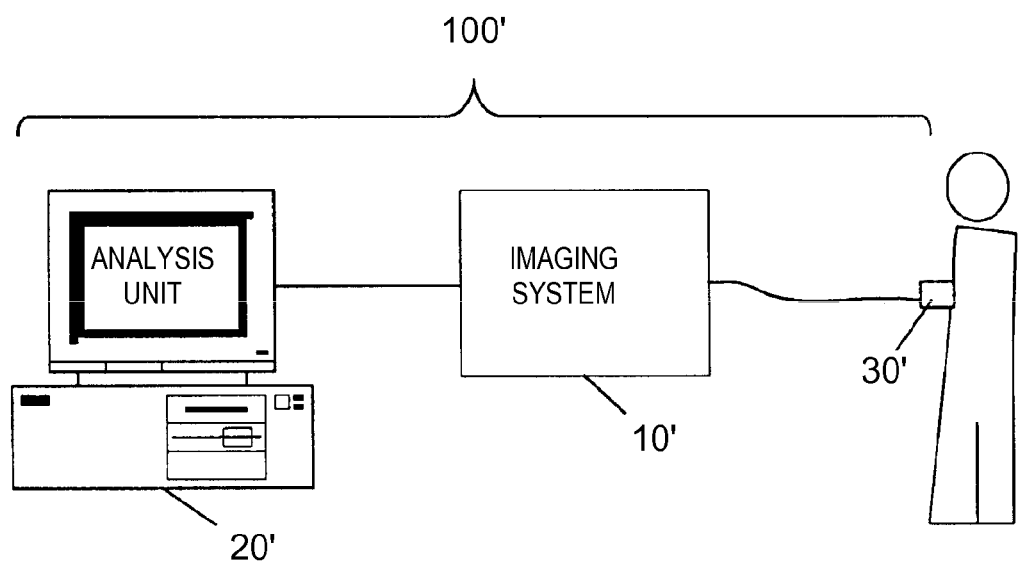
FIG. 18 schematically illustrates the main elements of the system according to a second embodiment of the present invention.

In a second and preferred embodiment of the present invention, and referring to FIG. 18, the system (100') also comprises a suitable ultrasonic imaging system (10') coupled to a suitable analysis unit (20'), as for the first embodiment. However, the ultrasonic system in the second embodiment is typically based on any suitable ultrasonic imaging system, and is characterized in being particularly adapted, or indeed dedicated, for providing image and motion data in the manner of the method of the present invention as described herein. The ultrasonic system according to the second embodiment typically comprises a selectable grey scale function capability. The depth range for this ultrasonic system is typically set at about 20 cm, for all patients, including adults, children and infants, with focal zone ranging from 2 cm to the end of the range. The frame acquisition rate is typically set at a minimum of 50 Hz, and is typically in the range of about 50 Hz to about 200 Hz, although the range could include higher rates than 200 Hz and or lower rates than 50 Hz.

The raw data provided by the ultrasonic system (10') is transmitted, typically via a suitable transducer having similar focus and depth capabilities as the ultrasonic system, to the analysis unit (20'). The data is stored in the analysis unit (20'), which is compatible with, and thus adapted for analyzing image data provided by the ultrasonic system (10'), in the manner of the method of the present invention, as described herein. It is also possible to incorporate the said ultrasonic imaging system (10') and the analysis unit (20') into a single unitary device or apparatus. Thus the present invention also relates to such a device or apparatus comprising a suitable ultrasonic imaging means (corresponding to the said ultrasonic imaging system (10')) coupled to or otherwise operatively connected to a suitable data analysis means (corresponding to the said analysis unit (20')), preferably integrated into a unitary device or apparatus.

Alternatively, according to the present invention an analysis unit (20') may be provided that is retrofittable with respect to, or capable of being coupled with, a suitable imaging system (10') that may already exist in a clinic or hospital ward, for example.

As with the first embodiment, the method of the second embodiment of the present invention, which is incorporated in the system and apparatus of the invention, is also based on the study of the dynamics of food boli within the esophagus by means of ultrasonic imaging, manipulation and analysis of such imaging. The dynamics of the boli as they traverse the esophagus, including direction and velocity of the boli, distance between boli, size of boli, are closely related to the esophageal function, i.e., to the dynamics of the peristaltic movement of esophagus itself.

As described above, and also in the second embodiment, the method of the present invention for evaluating or monitoring esophageal function of a patient, may be applied to a patient when the patient is in the process of swallowing at least one food bolus via the esophagus, and comprises the following steps:

(j) acquiring ultrasonic image data of at least one bolus at a plurality of temporal intervals as said food bolus passes through the esophagus;

(k) tracking said at least one bolus in said image data to identify esophagus and bolus image data corresponding to the bolus and to said esophagus in said image data;

(l) determining at least one esophagus function parameter from the said bolus and esophagus image data.

Thus, while the method is preferably carried out in a non-invasive manner when the patient is in the course of eating a regular meal, thus requiring a minimum of compliance, it is also possible to perform the method at other times, wherein the above steps are simply preceded by the patient swallowing at least one bolus of food, which can then form the basis of the imaging and analysis of the steps (a) to (c).

According to the second embodiment of the present invention, in step (a), ultrasonic images are acquired by the ultrasonic imaging system as the bolus or boli pass through the esophagus. Preferably, the ultrasonic imaging system (10') (or ultrasonic imaging means) comprises a suitable ultrasonic transducer (30') that is aligned with the esophagus. As the boli pass through the esophagus, image data of the part of the body covered by the transducer is recorded at relatively small time intervals ($t_i$), typically every 20 msec or less. At each time interval, the image data contains spatial information of bolus within the esophagus, as well as image data corresponding to other organs of the body, including, for example, the heart, spinal column and so on, typically as a grid of pixels of varying intensity. In this way, a cineloop containing image data with respect to time is acquired.

Thus, in step (a), spatial and dynamic data is acquired at discrete time intervals of 20 msec or less, and this data is stored in the analysis means (20') of the system (100').

As will be described in greater detail below, in step (b) the boli are tracked within the image data acquired in step (a) so that image data corresponding to the boli and to the esophagus (which is itself not directly visible to any great degree) may be identified within the overall image data, at each time interval.

In step (c), the image data acquired in (b) relating to the boli and/or esophagus is manipulated and analysed to determine the esophageal function of the esophagus being studied, and this preferably takes the form of calculating certain standardized esophageal function parameters, including:—

Net direction of travel of the boli, i.e. antegrade or retrograde or non-propulsive.

Average velocity of boli within the esophagus. This refers to both the average velocity of any particular bolus during passage thereof in the esophagus, and also the average velocity between a number of consecutive boli swallowed during one data acquisition session.

Average distance and/or time interval between consecutive boli swallowed during one data acquisition session.

Acceleration of antegrade and retrograde propagation of the boli. This is useful for assessment of esophageal strictures and in evaluation of reflux.

Step (b) and step (c) are typically performed off-line, that is after data acquisition of step (a) has been completed, and the operator may interact as desired with the stored raw image data.

Figure 19:
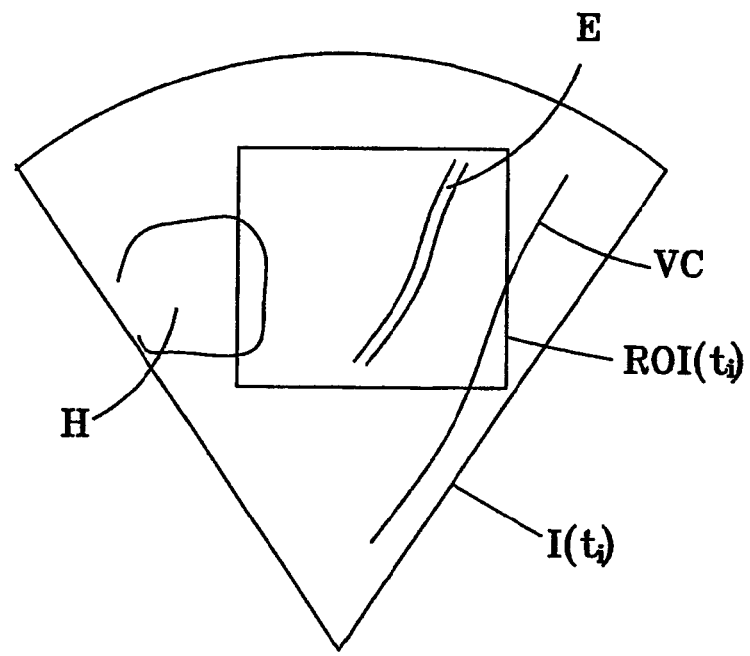
FIG. 19 schematically illustrates typical image data obtained at any particular time interval using the system in FIG. 18.

Step (b), off-line, generally takes the following form. Referring to FIG. 19, the image data ($I(t_i)$) taken in step (a) at any given time interval is visually inspected by the operator, and the general area comprising the esophagus (E) is identified, together with other organs such as the heart (H) and the spinal column (VC). Identification of the esophagus itself in any great detail is not possible directly, but rather in conjunction with the bolus trajectory data, as will become clearer herein. The raw ultrasonic data thus obtained may comprises a proportion of data (for example relating to the spinal column) that is not generally important to the analysis of the esophageal function, and is best disregarded.

In one problem usually encountered when trying to analyse such image, the motion of organs such as the heart generally applies a global pulsating motion to the esophagus, and this is preferably compensated for prior to analysis of the bolus dynamics. It is clearly not efficient to conduct such compensation on image data that is not relevant, for example relating to parts of the body that are of no interest to the investigation.

Thus, firstly, and referring to FIG. 19, the operator marks a rectangular (or any other shaped) region in the ultrasonic image previously obtained in step (a) at one particular time interval, typically the first scan, and this region is known as the region of interest (ROI), which contains the esophagus (E) and typically part of the heart (H) or another organ which moves with the esophagus in substantially the same manner thereto, and which has a relatively good contrast with the background image, as will be described in greater detail below. Any suitable method may be used for marking the ROI, such as for example by means of a cursor. The region of interest ($ROI(t_i)$) of the raw ultrasonic image data, taken at each time interval ($t_i$) is then separated from the full raw image data ($I(t_i)$) at that interval, by any suitable means, such as for example standard graphic programs. The ROI should preferably be chosen such that the esophagus and at least a part of the heart or other suitable reference zone appears in all the ROI's that are thus separated from the original raw data, i.e., during the full elapsed time period in which image data was collected.

Optionally, the actual ultrasonic transducer (30') may be adapted for providing image data of a smaller window of the body, including only the general area of the esophagus and part of the heart, for example, and with the smaller, but more useful field of data, a higher acquisition rate, say 300 Hz may be possible, yielding more accurate results.

Figure 20:
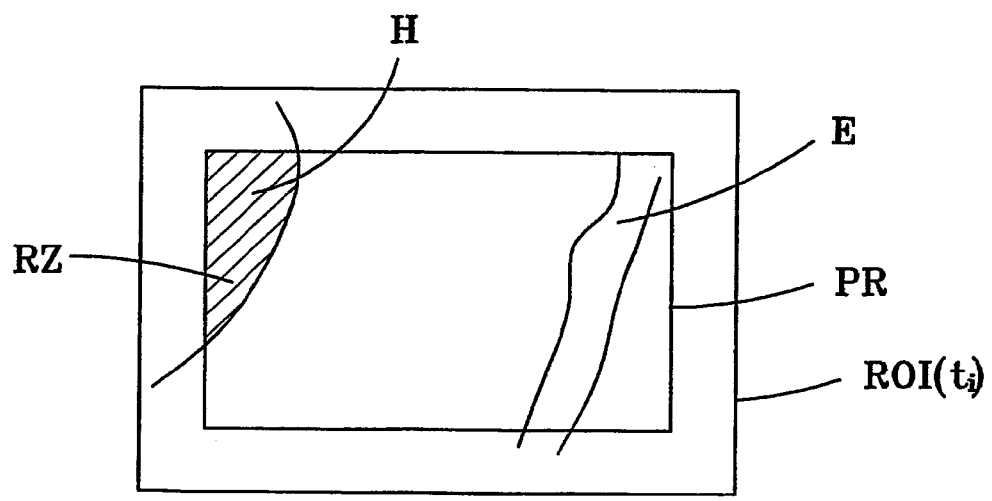
FIG. 20 schematically illustrates the relationship between the region of interest image data and the primary region image data.

The global motion associated with the esophagus is then determined. However, the esophagus itself, particularly the esophageal wall, has very poor contrast with respect to surrounding tissues, and thus cannot be readily identified. To overcome this difficulty, a basic assumption is made in that in the image data there exist at least one reference zone (RZ) that is moving together with the esophagus substantially as a rigid body, and that the actual relative movement between the esophagus and the said reference zone is thus negligible. Such a reference zone is also chosen to have relatively good contrast with respect to the surrounding tissues. A primary region is then chosen within the ROI that comprises such a reference zone, as illustrated in FIG. 20.

As already discussed, the esophagus is not easily discernible in the image data. Nevertheless, if the image data is viewed in the correct temporal sequence as a cineloop, the motion of the bolus through the esophagus identifies the general region of the esophagus by highlighting the position of various parts of the esophagus in turn, as the bolus passes through these parts. This enables the operator to choose a suitable primary region having a reference zone that is more visible and that has good contrast with the background, and that also moves with the global motion of the esophagus. As mentioned above, part of the heart wall serves as a reasonably good reference zone.

Thus, after reviewing the full cineloop of the original raw image data, or preferably of the ROI only, the operator manually selects the most appropriate primary region (PR) for a particular time interval, i.e. for a particular frame, typically the first image of the ROI images, such that most closely follows the global motion of the esophagus. Referring to FIG. 20, such primary regions (PR) may comprise, for example a part of the heart as a reference zone (RZ), and typically but not necessarily also at least a part of the esophagus (E).

Figure 21:
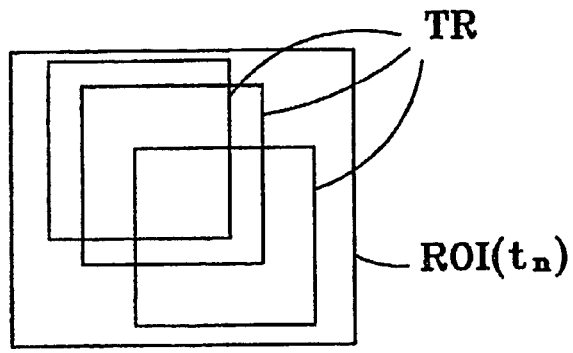
FIG. 21 schematically illustrates a number of possible test regions within a region of interest.

For ease of analysis, the primary region (PR) is rectangular in shape, though any other suitably-shaped region may be chosen. The primary region (PR) is marked off in any suitable manner, typically by means of a cursor. The next task is to find in the subsequent ROI images a corresponding region that most resembles the primary region of the first frame. Any suitable method may be employed for doing so. For example, and referring to FIG. 21, at each subsequent data point in the time domain, the corresponding ROI image data, $(ROI(t_n))$, is divided into a number of test regions (TR), of identical shape and size to the primary region (PR), that it is possible to fit separately in the corresponding ROI image data, and the properties of each such possible test region are compared to the properties of primary region (PR) of the first frame of ROI data. Typically, a method such as minimizing the SAD (Sum of Absolute Differences) may be employed to choose the test region that is closest to the primary region of the first frame, and this choice may be cross-checked by estimating the correlation coefficient between the original primary region (PR), and the best fit test region of the subsequent frames. In the SAD analysis of a test region, the intensity of each pixel in the primary region of the first ROI frame is compared with the intensity of a corresponding pixel that is in the same relative position within the test region, and the overall sum of the absolute differences in intensities between each pair of corresponding pixels is computed. The actual test region (TR) that provides the minimizes value for this SAD is deemed to be the closest to the original primary region (PR), and if the corresponding correlation coefficient is also sufficiently high, say about 0.6 or greater, it is assumed that the primary region has now moved to the location of this test region in this frame. Thus, the global movement between the first frame and this frame is determined. The same procedure is applied to each subsequent ROI frame, comparing each time the test regions of the ROI image of this frame with the primary region of the ROI image of the first frame to obtain the corresponding primary region location within each subsequent frame. While this is preferable, it is alternatively possible to repeat the procedure in a different manner, wherein, for example, for each subsequent frame, the ROI image for each frame is compared with any desired other fixed or variable frame. In the latter case, the frame immediately preceding the frame being analysed may be used as a datum frame, rather than a common frame for all subsequent frames, for example.

Figure 22:
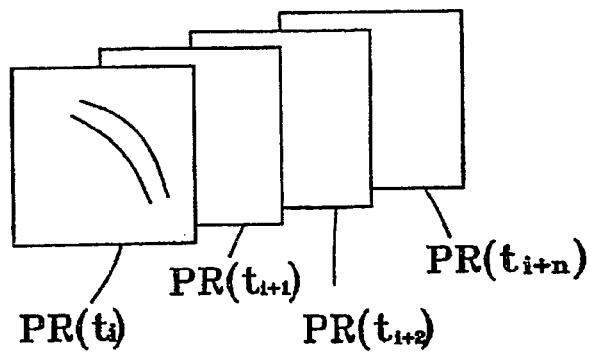
FIG. 22 schematically illustrates a succession of primary region images, after global compensation of the corresponding region of interest images.

In this manner, the manner in which the primary region effectively moves around the ROI from frame to frame, that is, with respect to the time domain, can be determined, and thus the global motion can be compensated accordingly. Typically, this compensation is performed by merely discarding all the image data outside of the primary region in each of the ROI frames, so that the remaining set of primary region images are aligned. Alternatively, each ROI image may be repositioned so that the primary regions in each image are aligned in the time domain. In other words, the aim of global compensation is to ensure as far as possible that the image of the esophagus is in the same position in each primary region $(PR(t_i))$, as illustrated in FIG. 22.

Figures 23, 24:
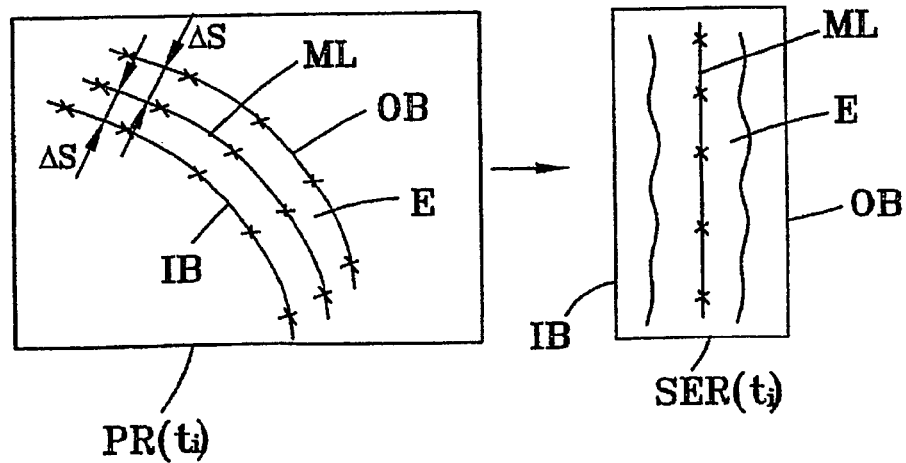
FIG. 23 illustrates the step of identifying and delineating the esophagus image data in the primary region of FIG. 22.
FIG. 24 schematically illustrates the projection of the esophagus image of FIG. 23 into a rectangular image.

Having substantially aligned the esophagus images by means of the primary regions $(PR(t_i))$, the next task is to separate out the actual image of the esophagus from each of the primary regions $(PR(t_i))$. Referring to FIG. 23, the operator manually marks out the approximate midline (ML) of the image of esophagus (E), which is typically curved. To facilitate this step, the sequence of primary region images may be run a few times, and the trajectory of the bolus as it passes through the esophagus noted. The general midline of this trajectory may then be marked by the operator, by means of a cursor, for example, and the sequence of images rerun with the midline (ML) marked thereon. If necessary, the midline (ML) may be shifted to better fit the said trajectory, and this procedure may be repeated several times until the operator is satisfied that the best midline possible has been achieved. In practice, it is possible for the operator to mark the said midline (MD) while the sequence of primary region images $(PR(t_i))$ may be run sequentially as en endless cineloop, which facilitates this task. Then, the outer boundary (OB) and inner boundary (IB) of the esophagus may be marked in a similar manner, typically by displacing the midline (MD) appropriately (in FIG. 23, generally upwardly and downwardly by $\Delta S$) such as to include the general width of the bolus that is identified in the primary regions $(PR(t_i))$. In this way, the trajectory of the bolus should be within the two boundaries (OB), (IB). Alternatively, the outer boundary (OB) or the inner boundary (IB) may be first marked off, and the remaining boundary and midline subsequently marked or determined automatically by suitably displacements therefrom.

Alternatively, it may be possible to automate the process of identifying the esophagus image data from the primary region images and marking the boundaries and midline of the esophagus. For example, once the sequence of primary region images $(PR(t_i))$ are available, they may be superimposed one over the other, and in general, the trajectory of the boli will now cover the full extent of the esophagus, appearing as a light area in contrast with the darker background in which the boli never pass. Thus, the lighter area will mark the approximate region of the esophagus, and any suitable graphics program can be used for automatically delineating the boundary of the light areas, i.e., IB and OB. Once the position of IB and OB are know, the midline between them, ML, can also be determined using any suitable graphics program.

In the next task, and referring to FIG. 24, the region delineated between the two boundaries (OB), (IB) (in FIG. 23) is preferably projected into an appropriate rectangle, herein referred to as a straightened esophageal region $(SER(t_i))$, by an appropriate transformation, which is a well known operation for which numerous graphic and other programs exist, and requires no further elaboration herein, effectively by straightening the midline (ML). This operation is repeated for each of the primary regions $(PR(t_i))$ to provide a series of straightened esophageal region $(SER(t_i))$ with respect to time, which when viewed consecutively show a substantially linear trajectory of the bolus.

Effectively, at this point step (b) has been completed: all the original raw image data in each image frame has been effectively filtered to retain only the image data corresponding to the passage of the bolus through the esophagus, this trajectory has been effectively straightened, and aligned with the other images to retain image data corresponding to the bolus and the esophagus.

Nevertheless, it is not strictly necessary to mark out the ROI's, and the above operations may be conducted without this step, mutatis mutandis. Further, other means for compensating for the global motion of the esophagus may be used, for example by tracking the motion of the heart wall, and using a control loop circuit to displace the ultrasonic probe in consonance with the heart wall, so that the esophagus data will be automatically aligned. Also, the sub step of straightening the esophagus image in FIG. 23 is not strictly necessary, and the analysis step (c) may be carried out on this image data, rather than the transformed image data of FIG. 24, in a similar manner to that described below for the SER, mutatis mutandis.

Step (c), analysis of the straightened esophageal region images (SER($t_i$)), can now be performed to obtain the esophageal parameters of interest. As with the first embodiment of the present invention, there are at least two different approaches to the analysis of the image data according to the second embodiment: focusing on the dynamics of a bolus as it traverses the esophagus, herein referred to as the "bolus analysis method"; focusing on a location or region of interest in the esophagus, herein referred to as the "regional analysis method".

Figure 25:
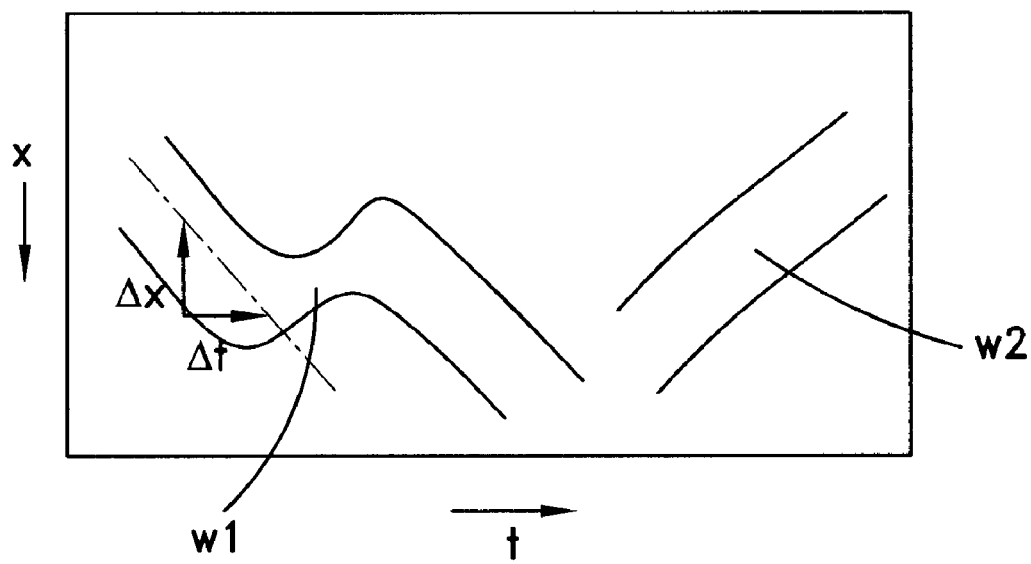
FIG. 25 schematically illustrates an M-mode display of a line of data of the image of FIG. 23 taken over time.

In the "bolus analysis method", for example, and as illustrated in FIG. 25, an M-mode display can now be provided, in which a one-dimensional image, a single A-line, corresponding to the midline (ML) for each of the straightened esophageal regions (SER($t_i$)), is displayed over time. Typically, the passage of a bolus is readily identified as a white band W1, in antegrade running from the top left to the bottom right. Often, some retrograde motion may also be detected as a zig-zag of the white band upwardly with respect to time. Reflux is identified as a white band running from the bottom left to the top right (W2), in all cases the top of the figure representing the entry to the esophagus, and the bottom of the figure the exit thereof to the stomach. Multiple boli in the esophagus are identified as multiple white streaks (not illustrated).

Thus, in this "bolus analysis method" according to the second embodiment, the slope of lighter areas in FIG. 25, that is, the distance $\Delta x$ covered by the bolus (vertical axis) over the time taken $\Delta t$ (horizontal axis) can be used to provide the average velocity of the bolus within the esophagus. This type of analysis provides information of how the esophagus as a whole is operating, since it follows the dynamics of one or more boli from the throat to the stomach, and thus esophageal parameters of interest are average bolus velocity (or transit time to stomach), smoothness of propagation of bolus through esophagus among others.

In the "regional analysis method", which focuses on a point or region in the esophagus, rather than on a specific bolus, general information may be obtained regarding the mode in which the esophagus is operating—antegrade, retrograde or non-propulsive. This form of analysis can also provide other information, such as velocity, acceleration experienced at various stations along the esophagus.

For example, and referring to FIG. 26($a$) and FIG. 26($b$), it may be desired to obtain esophageal parameters at three stations within the esophagus, near the throat (A), near the stomach (C) and at an intermediate location (B). At each station, a control region of interest (CR) is identified at the beginning of the analysis, and the properties of this image noted. Preferably, the control region (CR) is rectangular for ease of analysis, and centered on the station, but any other suitably shaped region may be used. In the subsequent time frame, i.e., after a time interval between frames of $\Delta t$, a corresponding region that most resembles the control region of the preceding frame is sought. Any suitable method may be employed for doing so. For example, and in a similar manner to the method employed above for determining the global movement of the esophagus, the straightened esophageal regions image data, (SER($t_n$)), is divided into a number of test regions of identical shape and size to the control region (CR) that it is possible to fit separately in the corresponding SER image data, and the properties of each such possible test region are compared to the properties of the control region (CR) of the preceding frame at the same station. Typically, a method such as minimizing the SAD (Sum of Absolute Differences) may be employed to choose the test region that is closest to the control region of the first frame, and this choice may be cross-checked by estimating the correlation coefficient between the preceding control region (CR), and the best fit test region of the frame being analysed. In the SAD analysis of a test region, the intensity of each pixel in the control region of the preceding frame is compared with the intensity of a corresponding pixel that is in the same position in the test region, and the overall sum of the absolute differences in intensities between all the corresponding pixels is computed. The actual test region that minimizes this SAD is deemed to be the closest to the control region (CR) of the preceding frame, and if the corresponding correlation coefficient is also sufficiently high, say about 0.6 or greater, it is assumed that the control region has now moved to the location of this test region, known as the optimal test region (OTR), in this frame. Thus, the effective displacement $\Delta d$ of the "bolus" contained in the control region between the first frame and this frame is determined, and since the time interval $\Delta t$ is also known, the corresponding velocity v may be computed from $v=\Delta d/\Delta t$.

Preferably, the above methodology for determining the optimal test region is conducted on a number of similar control region images located at the same station, but laterally, and possibly also slightly longitudinally, displaced with respect to one another, as illustrated in FIG. 26($a$). For each of the control regions ($CR_{Ai}$) at station A, for example, the optimal test region (OTR) corresponding thereto in the subsequent frame is determined, as well as the corresponding correlation coefficient of each OTR. Then, a weighted averaged displacement may be determined by averaging the displacements of the individual OTR's, weighted according to the correlation coefficients of the OTR's. Similar procedures may be effected at stations B and C.

The same procedure may now be applied at each of the stations in this frame, assessing the properties of the control region images at A, B, and C, and locating similar regions in the subsequent image frame to determine how the velocity has changed at these stations between the second and third image frames. Referring to FIG. 26($a$) and FIG. 26($b$), the control region images at A, B, and C, designated as ($CR_A$), ($CR_B$) and ($CR_C$), are found to have moved by a displacement of $\Delta d1$, $\Delta d2$ and $\Delta d3$, respectively, to positions ($OTR_A$), ($OTR_B$) and ($OTR_C$), respectively, after time $\Delta t$, wherein at A and B the displacement is positive, implying antegrade flow, and at C the displacement is negative, implying retrograde flow.

Similarly, the procedure is repeated for each successive pair of frames, comparing each time the test regions of the straightened esophageal regions (SER(t+$\Delta t$)) of the subsequent frame with the corresponding control region of the straightened esophageal regions (SER(t)) of the preceding frame (at each station A, B, C) to obtain the position, and thus displacement, of the corresponding control regions in the subsequent frame. In this manner, the velocity profile at each of the stations A, B and C may be computed as a function of time, as illustrated in FIG. 27. Typically, a suitable smoothing spline technique may be used for obtaining velocity values at pints along the esophagus between stations and for reducing the effects of noise.

In the type of velocity-time distributions illustrated in FIG. 27, each high velocity peak represents a bolus passing through station A, B or C in the esophagus. In each of the velocity distributions, by integrating the area in the distribution between successive peaks, marked for example as (p) and (q) for station A, a measure of the distance between successive boli can be approximated, and thus provides a measure of the wavelength or the inter-wave distance of the peristaltic waves at this station. Similar analyses may be conducted at other points or stations in the esophagus to obtain a broader picture of the esophageal function.

Further, once the velocity profile at any station is known with respect to time, this data may be numerically differentiated to provide the corresponding acceleration profile at this station.

The present invention also relates to any number of comparative methods for assessing the effect of any particular factor on the esophageal function of a patient, comprising:— evaluating the esophageal function of said patient according to the method described herein, in particular the first or second embodiments thereof, wherein said food bolus initially swallowed by the patient conforms to a first condition;

repeating step (i) with the same method, but wherein the food bolus is now swallowed by the patient conforming to a second condition;

comparing the results obtained between steps (i) and (ii).

The factor may include, for example, added medication, a new foodstuff, the position of the patient, and so on.

Thus, the present invention also relates to a comparative method for assessing the effect of added medication on the esophageal function of a patient, comprising:—

(i) evaluating the esophageal function of said patient according to the method described herein, in particular the first or second embodiments thereof, wherein said food bolus initially swallowed by the patient does not comprise said added medication;

(ii) repeating step (i) with the same method, but wherein the food bolus now swallowed by the patient comprises said added medication;

(iii) comparing the results obtained between steps (i) and (ii).

In this comparative method, the added medication may include any suitable medication, for example at least one anti reflux medication.

Also, the present invention also relates to a comparative method for assessing the effect of particular foodstuffs on the esophageal function of a patient, comprising:—

(i) evaluating the esophageal function of said patient according to the method described herein, in particular the first or second embodiments thereof, wherein said food bolus initially swallowed by the patient comprises a datum foodstuff;

(ii) repeating step (i) with the same method, but wherein the food bolus now swallowed by the patient replaced by a bolus of the foodstuff being investigated;

(iii) comparing the results obtained between steps (i) and (ii).

In this comparative method, the foodstuff being investigated may include a new milk formula or cereal, for example.

Also, the present invention also relates to a comparative method for assessing the effect of the position of the patient on the esophageal function of the patient, comprising:—

(i) evaluating the esophageal function of said patient according to the method described herein, in particular the first or second embodiments thereof, wherein said food bolus is initially swallowed by the patient while in a first position;

(ii) repeating step (i) with the same method, but wherein the food bolus of preferably the same type of food is now swallowed by the patient while in a second position;

(iii) comparing the results obtained between steps (i) and (ii).

In this comparative method, the first and second positions may include any one of sitting, lying down, standing, bending over, and so on.

Particularly in view of the excellent results of the clinical trials described hereinabove, the following statements about the present invention can be made:

Esophagography according to the present invention is non-invasive.

Cooperation of the patient is not strictly required. If necessary, a test can be delayed until such time as the patient swallows food in a normal manner.

The method of the invention may be performed bedside, using portable ultrasonography or echocardiography equipment.

As opposed to the conventional tests (e.g. manometry), sedation is not required.

Doppler Esophagography is obtained by using a regular meal, without the interference of invasive equipment which influences the normal esophageal motility.

Doppler Esophagography directly describes esophageal motility instead of measuring indirect variables such as esophageal acidity.

The present method identifies reflux episodes regardless of their acidity, in contrast to pH-metry; and in this aspect may be more sensitive than pH-metry.

Even for the most sensitive patients, those of the age group of the study, no adverse effect was noted or reported by parents or maternity unit staff.

Esophagography may be repeated as needed for follow-up or for the evaluation of treatment efficacy.

Image acquisition (according to the second embodiment) may be performed at substantially any angle with respect to the esophagus of the patient, so long as the passage of the bolus may be tracked in the images thus obtained. This represents an advantage over the first embodiment, in which the ultrasonic transducer has to be aligned with a viewing angle of substantially less than 90°, in practice substantially less than 45°, with respect to the esophagus axis so as to enable Doppler velocity measurements of the bolus to be made.

Although embodiments of the invention have been described by way of illustration, it will be understood that the invention may be carried out with many variations, modifications, and adaptations, without departing from its spirit or exceeding the scope of the claims.

BIBLIOGRAPHY

1. Nurko S, Esophageal Motility In: Walker W A, ed. Pediatric Gastrointestinal Disease, Philadelphia: Decker; 1991:224-235.
2. Tygat G N J, Gastro-Oesophageal Reflux and Gastric Stasis, Chester: Adis International; 1991.
3. Taber I, et, al., Mechanism of gastroesophageal reflux in healthy premature infants, Journal of Pediatrics, 1998:650-655.
4. Yamazaki N, Principle of Doppler Tissue Velocity Measurements, In: Erbel R, Nesser H J, Drozdz J, eds. Atlas of Tissue Doppler Echocardiography, Germany: Springer Press; 1995.
5. Strobel C T, Byrne W J, Ament M E, Euler A R, Correlation of esophageal lengths in children with height. Application to the Tuttle Test without prior esophageal manometry, J Pediatr. 1979;94:81-85.
6. Gryboski J, The swallowing mechanism of the neonate; Esophageal and gastric motility, Pediatrics, 1965;35:445-452.
7. Gomes H, Lallemand A, Lallemand P, Ultrasound of the gastroesophageal junction, Ped Radiol, 1993;23:94-99.
8. Hirsch W, Keda R, Preiss U, Color Doppler in the diagnosis of gastroesophageal reflux in children: comparison with pH measurements and B-mode ultrasound, Pediatr Radiol. 1996;26:232-235.
9. Jang H S, Lee S J, Lim G Y, Choy B G, Choi G H, Park H S, Correlation of color Doppler sonographic findings with pH measurements in gastroesophageal reflux in children, J Clin Ultrasound 2001;29:212-217.

10. Takebayashi 5, Matsui K, Ozawa Y, Nozawa T, Fujioka E. Cervical Esophageal motility: Evaluation with ultrasound in progressive systemic sclerosis, Radiology. 1991;179: 389-393.

What is claimed is:

1. An external, non-invasive method for monitoring passage of at least one food bolus through an esophagus whereby to evaluate esophageal function of a patient, comprising the steps:
   (a) non-invasively placing proximate an outside surface of the patient at least one ultrasonic transducer;
   (b) acquiring, from said ultrasonic transducer, ultrasonic image data of said at least one bolus at a plurality of temporal intervals as said at least one bolus passes through the esophagus after being swallowed by the patient;
   (c) tracking said at least one bolus in said image data to identify esophagus and bolus image data corresponding to said bolus and to said esophagus in said image data by;
      (1) determining global motion of the esophagus in the image data acquired in step (b):
      (2) aligning image data in consecutive image data by correcting for the global motion determined in step (c)(1); and
      (3) identifying esophagus image data by first identifying a position of the bolus image in successive images corresponding to the bolus traversing the esophagus; and
   (d) determining at least one esophagus function parameter from the said bolus and esophagus image data.

2. A method as claimed in claim 1, wherein step (c)(1) is preceded by the step of choosing a region of interest in said image data acquired in step (b) wherein step (c)(1) is performed on the region of interest image data.

3. A method as claimed in claim 2, wherein step (c)(1) is performed by determining the global motion of a reference zone of the image data at said plurality of temporal intervals.

4. A method as claimed in claim 3, wherein said reference zone is such that there is relatively insignificant relative movement between said reference zone and said esophagus in said image data.

5. A method as claimed in claim 1, further comprising the step:
   (c)(4) projecting the esophagus image data identified in step (c)(3) to a polygonal image matrix.

6. A method as claimed in claim 5, wherein said polygonal image matrix is in a form of a rectangle.

7. A method as claimed in claim 5, wherein step (d) comprises the sub-steps:
   (d)(1) obtaining one-dimensional image data corresponding to a line of the esophagus image data obtained in step (c)(4) for each esophagus image data along said plurality of temporal intervals;
   (d)(2) constructing an M-mode representation of the data provided in step (d)(1); and
   (d)(3) identifying trajectories of boli in said M-mode representation and determining at least one esophagus parameter therefrom.

8. A method as claimed in claim 7, wherein in step (d)(1) said line is a midline of said esophagus image data.

9. A method as claimed in claim 7, wherein said esophagus parameter is a velocity of said at least one bolus.

10. A method as claimed in claim 5, wherein step (d) comprises the sub-steps:
    (d)(1) choosing at least one station along one said esophagus image data frame;
    (d)(2) choosing at least one control zone at said at least one station;
    (d)(3) identifying a control zone in a subsequent esophagus image data frame having closest image data to said at least one control zone of said at least one station in step (d)(2);
    (d)(4) determining displacement of the control zone in step (d)(2) and the control zone identified in step (d)(3); and
    (d)(5) determining at least one esophagus parameter therefrom and/or from a time interval between said image data frame and said subsequent image data frame.

11. A method as claimed in claim 10, wherein said esophagus parameter is a velocity of said at least one bolus.

12. A method as claimed in claim 11, wherein another said esophagus parameter is an acceleration of said at least one bolus.

13. A method as claimed in claim 10, wherein step (d)(3) is performed by means of minimizing a SAD (Sum of Absolute Differences) between an image of the control zone in (d)(2) and an image of the control zone identified in step (d)(3).

14. A method as claimed in claim 10, wherein steps (d)(1) to (d)(5) are performed for each consecutive pair of esophagus image frames along a time domain.

15. A method as claimed in claim 1, wherein in step (b) said image data further comprises dynamic image data for each of said temporal intervals.

16. A method as claimed in claim 15, wherein said dynamic image data comprises Doppler velocity and is acquired by means of a Doppler technique.

17. A method as claimed in claim 15, wherein in step (c) bolus image data is identified by determining higher velocity regions of the image data.

18. A method as claimed in claim 17, wherein said higher velocity regions are visualized using a colour-coded tissue velocity imaging technique.

19. A method as claimed in claim 15, wherein step (d) is performed substantially in real-time.

20. A method as claimed in claim 15, wherein step (d) is performed in off-line.

21. A method as claimed in claim 15, wherein step (c) is carried out for a first portion of image motion data in step (b) corresponding to an imaginary axis within said image motion data recorded at each said time interval to provide velocity data along said axis.

22. A method as claimed in claim 21, wherein said imaginary axis is substantially aligned with a longitudinal axis of the esophagus.

23. A method as claimed in claim 22, wherein said first portion of said image motion data corresponding to said imaginary axis is compiled from each consecutive image data obtained at consecutive time intervals in step (b) to provide velocity data along said axis as a function of time.

24. A method as claimed in claim 23, wherein a position and trajectory of a bolus along said axis with respect to time is correlated to portions of said velocity data having relatively higher magnitudes of velocity among said velocity data.

25. A method as claimed in claim 24, wherein average velocity of a bolus along said axis is determined by identifying the trajectory of the bolus in said velocity data and providing the quotient of: (distance covered by the bolus along said axis) divided by (the corresponding time taken by the bolus).

26. A method as claimed in claim 25, wherein the position and trajectory of a number of consecutive boli along said axis with respect to time is correlated to corresponding portions of said velocity data having higher magnitudes of velocity among said velocity data.

27. A method as claimed in claim 26, wherein inter-bolus distance and or inter boli time interval along said axis is determined by identifying the trajectory of two consecutive boli in said velocity data and providing the distance between the two trajectories at any particular time interval within these trajectories.

28. A method as claimed in claim 16, wherein step (c) is carried out for a second portion of image motion data in step (b) corresponding to at least one predetermined location within said image motion data recorded at each said time interval to provide velocity data at said location.

29. A method as claimed in claim 28, wherein said at least one predetermined location is located substantially on a longitudinal axis of the esophagus.

30. A method as claimed in claim 29, wherein said second portion of said image motion data corresponding to said location is compiled from each consecutive image data obtained at consecutive time intervals in step (b) to provide velocity data at said location as a function of time.

31. A method as claimed in claim 30, wherein direction and velocity of boli passing through said location with respect to time is correlated to portions of said velocity data having relatively higher magnitudes of velocity among said velocity data.

32. A method as claimed in claim 31, wherein peak velocity of a bolus passing through said location is determined by identifying a corresponding velocity peak in said velocity data.

33. A method as claimed in claim 32, wherein a mode of propagation of a number of consecutive boli at said location with respect to time is correlated to an integral of the velocity data with respect to time.

34. A method as claimed in claim 33, wherein the mode of propagation of the esophagus is antegrade mode, retrograde mode and non-propulsive modes, according to whether the said integral is substantially positive, negative or zero, respectively.

35. A method as claimed in claim 15, wherein said ultrasonic image motion data in step (b) is procured using a tissue velocity imaging technique.

36. A method as claimed in claim 1, wherein said at least one esophagus function parameter comprises at least one, preferably more than one and more preferably all of the following: propagation direction, inter-boli time interval, inter-boli space interval, velocity and acceleration of peristaltic waves.

37. A method as claimed in claim 1, wherein at least one bolus is liquid, and thus substantially incompressible, wherein the boli propagation, inter-bolus time interval, and velocity are particularly closely related to equivalent peristaltic wave characteristics of an esophageal wall.

38. An external, non-invasive comparative method for assessing an effect of a predetermined factor on esophageal function of a patient, comprising:
 (i) evaluating the esophageal function of said patient by following the steps:
  (a) non-invasively placing proximate an outside surface of the patient at least one ultrasonic transducer;
  (b) acquiring, from said ultrasonic transducer, ultrasonic image data of at least one bolus at a plurality of temporal intervals as said at least one bolus passes through the esophagus after being swallowed by the patient;
  (c) tracking said at least one bolus in the image data to identify esophagus and bolus image data corresponding to said bolus and to said esophagus in said image data by;
   (1) determining global motion of the esophagus in the image data acquired in step (b);
   (2) aligning image data in consecutive image data by correcting for the global motion determined in step (c)(1); and
   (3) identifying esophagus image data by first identifying a position of the bolus image in successive images corresponding to the bolus traversing the esophagus; and
  (d) determining at least one esophagus function parameter from the said bolus and esophagus image data,
 wherein said bolus initially swallowed by the patient conforms to a first condition;
 (ii) repeating step (i), but wherein the bolus is now swallowed by the patient conforming to a second condition; and
 (iii) comparing results obtained between steps (i) and (ii).

39. An external, non-invasive comparative method for assessing an effect of added medication on esophageal function of a patient, comprising:
 (i) evaluating the esophageal function of said patient by following the steps:
  (a) non-invasively placing proximate an outside surface of the patient at least one ultrasonic transducer that is aligned substantially with a longitudinal axis of the esophagus of the patient;
  (b) acquiring, from said ultrasonic transducer, ultrasonic image data of at least one bolus at a plurality of temporal intervals as said at least one bolus passes through the esophagus after being swallowed by the patient;
  (c) tracking said at least one bolus in the image data to identify esophagus and bolus image data corresponding to said bolus and to said esophagus in said image data by;
   (1) determining global motion of the esophagus in the image data acquired in step (b);
   (2) aligning image data in consecutive image data by correcting for the global motion determined in step (c)(1); and
   (3) identifying esophagus image data by first identifying a position of the bolus image in successive images corresponding to the bolus traversing the esophagus; and
  (d) determining at least one esophagus function parameter from the said bolus and esophagus image data,
 wherein said bolus of step (b) does not comprise said added medication;
 (ii) repeating step (i), wherein the bolus of step (b) now comprises said added medication; and
 (iii) comparing results obtained between steps (i) and (ii).

40. A method as claimed in claim 39, wherein said added medication includes at least one anti-reflux medication.

41. An external, non-invasive comparative method for assessing an effect of particular foodstuffs on esophageal function of a patient, comprising:
 (i) evaluating the esophageal function of said patient by following the steps:
  (a) non-invasively placing proximate an outside surface of the patient at least one ultrasonic transducer that is aligned substantially with a longitudinal axis of the esophagus of the patient;
  (b) acquiring, from said ultrasonic transducer, ultrasonic image data of at least one bolus at a plurality of temporal intervals as said at least one food bolus passes through the esophagus after being swallowed by the patient;

(c) tracking said at least one bolus in the image data to identify esophagus and bolus image data corresponding to said bolus and to said esophagus in said image data by;
   (1) determining global motion of the esophagus in the image data acquired in step (b);
   (2) aligning image data in consecutive image data by correcting for the global motion determined in step (c)(1); and
   (3) identifying esophagus image data by first identifying a position of the bolus image in successive images corresponding to the bolus traversing the esophagus; and
(d) determining at least one esophagus function parameter from the said bolus and esophagus image data,
wherein said bolus initially swallowed by the patient comprises a datum foodstuff
   (ii) repeating step (i) but wherein the bolus now swallowed by the patient replaced by a bolus of the particular foodstuff being investigated; and
   (iii) comparing results obtained between steps (i) and (ii).

42. A method as claimed in claim 38, wherein the particular foodstuff being investigated includes a new milk formula or cereal.

43. An external, non-invasive comparative method as claimed in claim 38, particularly for assessing an effect of a position of the patient on the esophageal function of the patient, comprising:
   (i) evaluating the esophageal function of said patient by following the steps:
      (a) non-invasively placing proximate an outside surface of the patient at least one ultrasonic transducer;
      (b) acquiring, from said ultrasonic transducer, ultrasonic image data of at least one bolus at a plurality of temporal intervals as said at least one bolus passes through the esophagus after being swallowed by the patient;
      (c) tracking said at least one bolus in the image data to identify esophagus and bolus image data corresponding to said bolus and to said esophagus in said image data by;
         (1) determining global motion of the esophagus in the image data acquired in step (b);
         (2) aligning image data in consecutive image data by correcting for the global motion determined in step (c)(1); and
         (3) identifying esophagus image data by first identifying a position of the bolus image in successive images corresponding to the bolus traversing the esophagus; and
      (d) determining at least one esophagus function parameter from the said bolus and esophagus image data,
   wherein said bolus is initially swallowed by the patient while in a first position;
   (ii) repeating step (i) but wherein the bolus is preferably a same type of food as in step (i) and is now swallowed by the patient while in a second position; and
   (iii) comparing results obtained between steps (i) and (ii).

44. A method as claimed in claim 43, wherein said first position and said second position include any one of sitting, lying down, standing, and bending over.

45. An external, non-invasive system for evaluating esophageal function of a patient, comprising:
   at least one ultrasonic transducer;
   an ultrasonic imaging system electrically coupled to the ultrasonic transducer;
   at least one analysis unit electrically coupled to the ultrasonic imaging system, characterized in that the at least one analysis unit is adapted for evaluating esophageal function by performing:
   (a) acquiring, from said ultrasonic transducer, which has been non-invasively placed proximate an outside surface of the patient, ultrasonic image data of at least one bolus at a plurality of temporal intervals as said at least one bolus passes through the esophagus after being swallowed by the patient;
   (b) tracking said at least one bolus in the image data to identify esophagus and bolus image data corresponding to said bolus and to said esophagus in said image data by;
      (1) determining global motion of the esophagus in the image data acquired in step (a);
      (2) aligning image data in consecutive image data by correcting for the global motion determined in step (b)(1); and
      (3) identifying esophagus image data by first identifying a position of the bolus image in successive images corresponding to the bolus traversing the esophagus; and
   (c) determining at least one esophagus function parameter from the said bolus and esophagus image data.

* * * * *